US009450119B2

United States Patent
Hasegawa et al.

(10) Patent No.: US 9,450,119 B2
(45) Date of Patent: Sep. 20, 2016

(54) BIBENZO[B]FURAN COMPOUND, PHOTOELECTRIC CONVERSION MATERIAL, AND PHOTOELECTRIC CONVERSION ELEMENT

(71) Applicant: ADEKA CORPORATION, Tokyo (JP)

(72) Inventors: Mineki Hasegawa, Tokyo (JP); Toru Yano, Tokyo (JP); Ryo Taniuchi, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 19 days.

(21) Appl. No.: 14/236,225

(22) PCT Filed: Oct. 22, 2012

(86) PCT No.: PCT/JP2012/077208
§ 371 (c)(1),
(2) Date: Jan. 30, 2014

(87) PCT Pub. No.: WO2013/061909
PCT Pub. Date: May 2, 2013

(65) Prior Publication Data
US 2014/0252278 A1    Sep. 11, 2014

(30) Foreign Application Priority Data

Oct. 24, 2011    (JP) ................................ 2011-232808

(51) Int. Cl.
*H01L 51/42*      (2006.01)
*H01L 31/0256*    (2006.01)
*C07D 493/06*     (2006.01)
*C08G 61/12*      (2006.01)
*H01L 51/00*      (2006.01)
*B82Y 10/00*      (2011.01)

(52) U.S. Cl.
CPC ........... *H01L 31/0256* (2013.01); *B82Y 10/00* (2013.01); *C07D 493/06* (2013.01); *C08G 61/125* (2013.01); *H01L 51/0036* (2013.01); *H01L 51/0043* (2013.01); *C08G 2261/1412* (2013.01); *C08G 2261/1424* (2013.01); *C08G 2261/312* (2013.01); *C08G 2261/3223* (2013.01); *C08G 2261/3241* (2013.01); *C08G 2261/3242* (2013.01); *C08G 2261/3246* (2013.01); *C08G 2261/3327* (2013.01); *C08G 2261/3328* (2013.01); *C08G 2261/344* (2013.01); *C08G 2261/364* (2013.01); *H01L 51/0047* (2013.01); *H01L 51/4253* (2013.01); *H01L 2031/0344* (2013.01); *Y02E 10/549* (2013.01)

(58) Field of Classification Search
CPC ..... C07D 493/06; C08G 61/12; H01L 51/42; H01L 31/00
USPC ....... 252/500; 549/60, 4; 548/126, 440, 453; 136/263
See application file for complete search history.

(56) References Cited

U.S. PATENT DOCUMENTS

| 8,158,275 | B2 | 4/2012 | Ie et al. | |
|---|---|---|---|---|
| 9,324,889 | B2 * | 4/2016 | Hanaya | ................ H01L 51/006 |
| 2008/0083455 | A1 | 4/2008 | Li et al. | |
| 2009/0240014 | A1 | 9/2009 | Ie et al. | |
| 2009/0292130 | A1 | 11/2009 | Shi et al. | |
| 2014/0299191 | A1 * | 10/2014 | Akimoto | .............. H01G 9/2059 136/263 |

FOREIGN PATENT DOCUMENTS

| CN | 101389634 | 3/2009 | |
|---|---|---|---|
| JP | 2008140989 | 6/2008 | |
| JP | 2009-158921 | 7/2009 | |
| JP | 2010018529 | 1/2010 | |
| JP | 2010-177634 | 8/2010 | |
| JP | 2011-116962 | 6/2011 | |
| JP | 2011-195566 | 10/2011 | |
| WO | WO 2015024848 A1 * | 2/2015 | ............. C09K 11/06 |

OTHER PUBLICATIONS

English translation of JP 20111195566, Oct. 6, 2011.*
International Search Report, PCT/JP2012/077208, Nov. 20, 2012.
Hui-Ming GE et al., Antioxidant Oligostilbenoids from the Stem Wood of Hopea hainanensis, Journal of Agricultural and Food Chemistry, 2009, vol. 57, No. 13, p. 5756-5761.
Padinger et al., "Effects of Postproducton Treatment on Plastic Solar Cells", Advanced Functional Materials, 2003, 13, No. 2 February.

* cited by examiner

*Primary Examiner* — Douglas McGinty
(74) *Attorney, Agent, or Firm* — Young & Thompson

(57) ABSTRACT

Disclosed is a p-type organic semiconductive material that is easy to produce and that has a high planarity in its polymer skeleton, and also provides a photoelectric conversion material, a photoelectric conversion layer, a photoelectric conversion element, and an organic thin film solar cell each having high photoelectric conversion efficiency and using the p-type organic semiconductive material. Specifically, the invention provides a bibenzo[b]furan compound having at least one constitutional unit represented by the following formula (1) or (2), as well as a photoelectric conversion material, a photoelectric conversion layer, a photoelectric conversion element, and an organic thin film solar cell each using that compound for a p-type organic semiconductive material. (In the formulae, $R^{13}$ and $R^{14}$ each represent a hydrogen atom, a fluorine atom, a chlorine atom, a bromine atom, an iodine atom, an optionally substituted hydrocarbon group, an optionally substituted hydrocarbonoxy group, or an optionally substituted heterocyclic group.)

8 Claims, 1 Drawing Sheet

BIBENZO[B]FURAN COMPOUND, PHOTOELECTRIC CONVERSION MATERIAL, AND PHOTOELECTRIC CONVERSION ELEMENT

TECHNICAL FIELD

The present invention relates to a novel p type organic semiconductive material having a specific structure, as well as a photoelectric conversion material and a photoelectric conversion element using the same.

BACKGROUND ART

In recent years, much consideration has been given to solar cells (solar electricity generation), which can be used continuously, which does not cause exhaustion of resources, and which hardly causes environmental pollution. Solar cells are classified roughly into inorganic solar cells, such as Si type and non-Si type, and organic solar cells, such as dye-sensitization type and organic thin film type. Inorganic solar cells are generally high in photoelectric conversion efficiency, but they are disadvantageously high in production cost because high vacuum is required or heat treatment at high temperatures is required. With organic solar cells, since a film can be formed by a coating process, a printing process, etc., their production cost is lower and films large in area can be produced. Additional advantage of organic solar cells over inorganic solar cells is that the former can afford elements lighter in weight. Particularly, since organic thin film type solar cells are more suitable for a printing process and are easy to be formed into film and the like, it has been reported that the production of flexible solar cells is easy.

However, many organic solar cells are low in photoelectric conversion efficiency, improvement in photoelectric conversion efficiency has been considered as a challenge.

Examples of materials with which high photoelectric conversion efficiency with organic thin film type solar cells has been achieved include a bulk heterojunction made of a mixed material made up of a p-type organic semiconductive material P3HT [poly(3-hexylthiophene] and an n-type organic semiconductive material PCBM [[6,6]-phenyl-C61-butylic acid methyl ester] (see, for example, Non-Patent Literature 1). Although small molecules such as pentacene are used as p-type organic semiconductive materials in some cases, polymer type materials are generally believed to be more suitable for the manufacture of elements by coating and therefore they are believed to be easier to achieve reduction in cost and enlargement in screen size.

One feature sought with p-type organic semiconductive materials is that a material has therein a highly planar π conjugated plane. This is because higher π-π interaction or higher carrier transfer efficiency are expected, and accordingly, high photoelectromotive force can be provided.

Patent Literatures 1 to 3 disclose polymer-type p-type organic semiconductors.

However, improvement in photoelectric conversion efficiency has been desired therewith more than organic solar cells.

CITATION LIST

Patent Literature

Patent Literature 1: U.S. Patent Application Publication No. 2008/0083455
Patent Literature 2: JP 2009-158921 A
Patent Literature 3: JP 2011-116962 A

Non-Patent Literature

Non-Patent Literature 1: F. Padinger, et al., Adv. Funct. Mater., 13, 85 (2003)

SUMMARY OF INVENTION

Technical Problem

Accordingly, an object of the present invention is to provide a p-type organic semiconductive material that is easy to produce and that has a high planarity in its polymer skeleton.

Another object of the present invention is to provide a photoelectric conversion material, a photoelectric conversion layer, a photoelectric conversion element, and an organic thin film solar cell each having high photoelectric conversion efficiency and using the above p-type organic semiconductive material.

Solution to Problem

As a result of earnest studies the present inventors found that a bibenzo[b]furan compound having a specific structure is easy to produce, requires a low production cost, and high in solubility and therefore a photoelectric conversion layer can be produced easily if the compound is used as a p-type organic semiconductive material. In addition, as a result of further studies, they found that a photoelectric conversion element using the photoelectric conversion layer exhibits a high carrier mobility and therefore can solve the above-mentioned problems.

The present invention has been devised on the basis of the above finding and provides a novel bibenzo[b]furan compound having at least one constitutional unit represented by the following formula (1) or (2) (henceforth also referred to as a first bibenzo[b]furan compound).

[Chemical Formula 1]

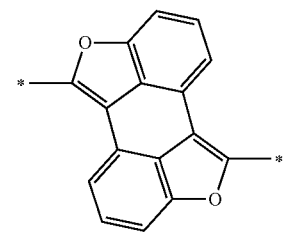
(1)

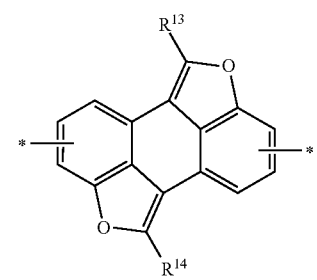
(2)

wherein $R^{13}$ and $R^{14}$ each represent a hydrogen atom, a fluorine atom, a chlorine atom, a bromine atom, an iodine atom, an optionally substituted hydrocarbon group, or an optionally substituted heterocyclic group.

The present invention also provides a photoelectric conversion material comprising (A) a p-type organic semiconductive material comprising at least one first bibenzo[b]furan compound and (B) an n-type organic semiconductive material.

The present invention also provides a photoelectric conversion layer obtained by forming the above photoelectric conversion material into a film.

The present invention also provides a photoelectric conversion element having the above photoelectric conversion layer.

The present invention also provides an organic thin film solar cell comprising the above photoelectric conversion element.

The present invention also provides a novel bibenzo[b]furan compound represented by the following formula (B1) or (B2) that is useful as an intermediate to the first bibenzo[b]furan compound (henceforth also referred to as second bibenzo[b]furan compound).

[Chemical Formula 1A]

(B1)

(B2)

wherein $R^{13}$ and $R^{14}$ each represent a hydrogen atom, a fluorine atom, a chlorine atom, a bromine atom, an iodine atom, an optionally substituted hydrocarbon group, or an optionally substituted heterocyclic group, $R^{21}$, $R^{22}$, $R^{23}$, and $R^{24}$ each represent a hydrogen atom, a fluorine atom, a chlorine atom, a bromine atom, or an iodine atom, X represents a group formed by combining 1 to 5 types of group selected the following Group X:

[Chemical Formula 2]

<Group X>

(X-1)

(X-2)

(X-3)

(X-4)

(X-5)

(X-6)

(X-7)

wherein $X^1$ and $X^4$ each represent S, O, or $NR^3$, $R^3$ represents an optionally substituted hydrocarbon group, any hydrogen atom in the constitutional units represented by Group X may be substituted with a fluorine atom, a chlorine atom, a bromine atom, an iodine atom, a cyano group, a nitro group, a hydroxyl group, a thiol group, an —$NR^4R^5$ group, an optionally substituted hydrocarbon group, or an optionally substituted heterocyclic group, $R^4$ and $R^5$ each represent an optionally substituted hydrocarbon group, k represents an integer of 1 to 4.

Advantageous Effects of Invention

According to the present invention, there can be provided a novel bibenzo[b]furan compound that can be produced at a low cost, is superior in solubility and coatability, and is useful as organic semiconductive materials. The use of a photoelectric conversion material of the present invention containing this compound makes a coating process in semiconductor production due to high solubility and can realize enhancement in the performance of an element due to high carrier mobility.

DESCRIPTION OF EMBODIMENTS

Figure 1A:
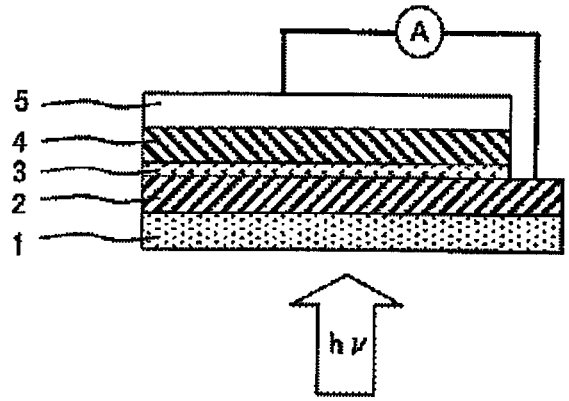
FIG. 1(a) is a cross-sectional view illustrating one example of the configuration of the photoelectric conversion element of the present invention.

The novel bibenzo[b]furan compounds of the present invention and their intermediates as well as photoelectric conversion materials, photoelectric conversion layers, photoelectric conversion layers, and organic thin film solar cells using the bibenzo[b]furan compounds are described in detail below on the basis of preferred embodiments.

First bibenzo[b]furan Compound

The first bibenzo[b]furan compound is any compound having at least one constitutional unit represented by the above formula (1) or (2). The mark * drawn in the above formula (1) or (2) means that the groups represented by these formulae are bound to the adjoining groups at the sites indicated by the * (the same is applied hereinafter).

Examples of the optionally substituted hydrocarbon group represented by $R^{13}$ and $R^{14}$ in the above formula (2) include aromatic hydrocarbon groups, aromatic hydrocarbon groups substituted with an aliphatic hydrocarbon, and aliphatic hydrocarbon groups; those having 1 to 40, especially 4 to 22, carbon atoms are preferred.

Examples of the aromatic hydrocarbon groups include phenyl, naphthyl, cyclohexylphenyl, biphenyl, terphenyl, fluorenyl, thiophenylphenyl, furanylphenyl, 2'-phenyl-propylphenyl, benzyl, and naphthylmethyl.

Examples of the aliphatic hydrocarbon groups include linear, branched, or cyclic alkyl groups such as methyl, ethyl, propyl, isopropyl, butyl, sec-butyl, tert-butyl, isobutyl, amyl, isoamyl, tert-amyl, hexyl, heptyl, isoheptyl, tert-heptyl, n-octyl, isooctyl, tert-octyl, nonyl, cyclopropyl, cyclobutyl, cyclopentyl, cyclohexyl, cycloheptyl, cyclooctyl, cyclononyl, and cyclodecyl, these aliphatic hydrocarbon groups may be interrupted by —O—, —COO—, —OCO—, —CO—, —S—, —SO—, —SO$_2$—, —NR$^{15}$—, —HC=CH—, or —C≡C— (such interruption may interrupt the part at which the aliphatic hydrocarbon group is bound), $R^{15}$ represents an optionally substituted hydrocarbon group, wherein examples of the optionally substituted hydrocarbon group include the same groups as the optionally substituted hydrocarbon groups represented by $R^{13}$ and $R^{14}$, and especially, perfluoroalkyl is preferred.

Examples of the aromatic hydrocarbon groups substituted with an aliphatic hydrocarbon include phenyl, naphthyl, benzyl, etc. substituted with the above-mentioned aliphatic hydrocarbon groups.

Examples of the group with which these hydrocarbon groups may be substituted include a fluorine atom, a chlorine atom, a bromine atom, an iodine atoms, a cyano group, a nitro group, a hydroxyl group, a thiol group, and an —NR'R" group, wherein R' and R" each represent an optionally substituted hydrocarbon group, examples of which include the same groups as the optionally substituted hydrocarbon groups represented by $R^{13}$ and $R^{14}$.

Examples of the optionally substituted heterocyclic group represented by $R^{13}$ and $R^{14}$ in the above formula (2) include heterocyclic rings such as thiazolyl, imidazolyl, oxazolyl, pyridyl, pyrazinyl, pyrimidinyl, pyridazinyl, thiophenyl, furanyl, bithiophenyl, and terthiophenyl; those having 1 to 40, especially 4 to 22, carbon atoms are preferred.

Of such first bibenzo[b]furan compounds, those having 2 to 100 constitutional units represented by the above formula (1) or (2) are preferred because of their superior film formability. First bibenzo[b]furan compounds may have a constitutional unit (henceforth also referred to as other constitutional units) other than the constitutional units represented by the above formula (1) or (2). When the first bibenzo[b]furan compound has such other constitutional units, the content of the constitutional units of the above formula (1) or (2) is preferably 5 to 100 mol %, more preferably 10 to 90 mol %, and particularly preferably 20 to 80 mol %.

Such other constitutional units are not particularly restricted as long as they are π-conjugated groups, and examples thereof include constitutional units selected from the following Group Y or Group Z; from the viewpoints of durability and photoresistance of the material, constitutional units selected from (Y-2), (Y-3), (Y-4) or Group Z are preferred,

[Chemical Formula 2A]

<Group Y>

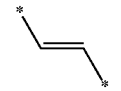
(Y-1)

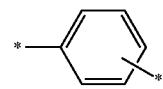
(Y-2)

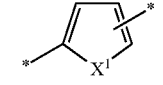
(Y-3)

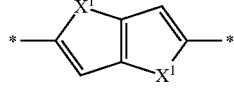
(Y-4)

(Y-5)

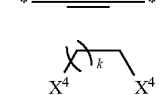
(Y-6)

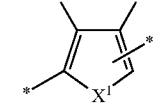
(Y-7)

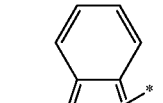
(Y-8)

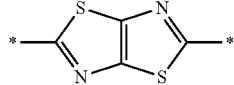

wherein $X^1$ and $X^4$ each represent S, O, or NR$^3$, k represents an integer of 1 to 4, $R^3$ represents an optionally substituted hydrocarbon group, any hydrogen atom in the constitutional units represented by Group Y may be substituted with a fluorine atom, a chlorine atom, a bromine atom, an iodine atom, a cyano group, a nitro group, a hydroxyl group, a thiol group, an —NR$^4$R$^5$ group, an optionally substituted hydrocarbon group, or an optionally substituted heterocyclic group, $R^4$ and $R^5$ each represent an optionally substituted hydrocarbon group,

[Chemical Formula 3]
<Group Z>
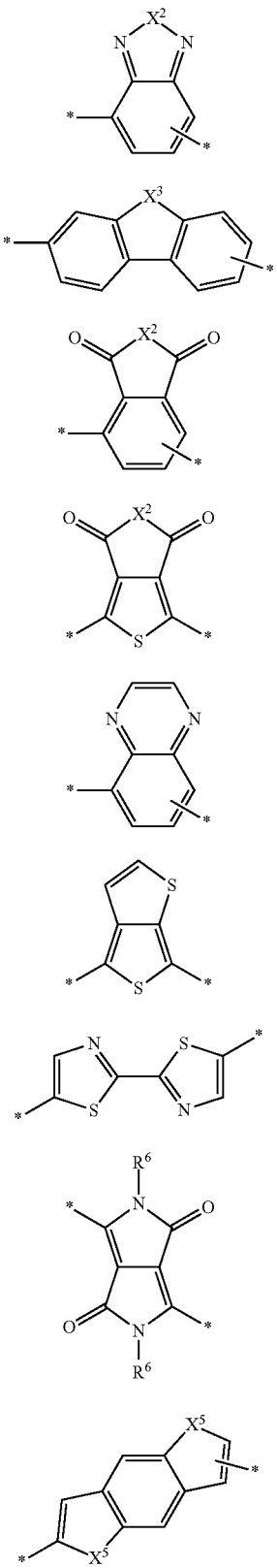
(Z-1)
(Z-2)
(Z-3)
(Z-4)
(Z-5)
(Z-6)
(Z-7)
(Z-8)
(Z-9)
-continued
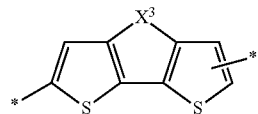 (Z-10)
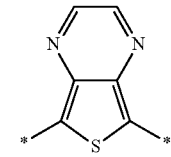 (Z-11)
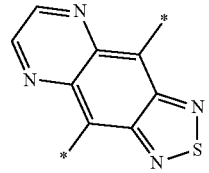 (Z-12)
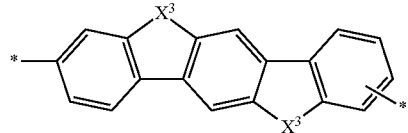 (Z-13)
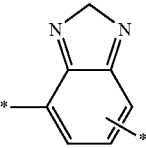 (Z-14)
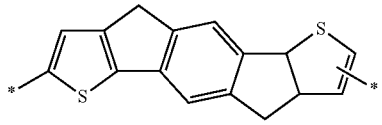 (Z-15)
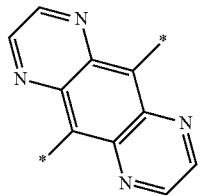 (Z-16)
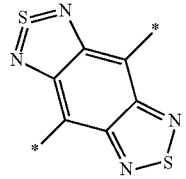 (Z-17)
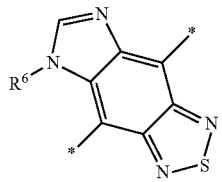 (Z-18)
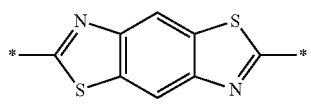 (Z-19)

-continued (Z-20)

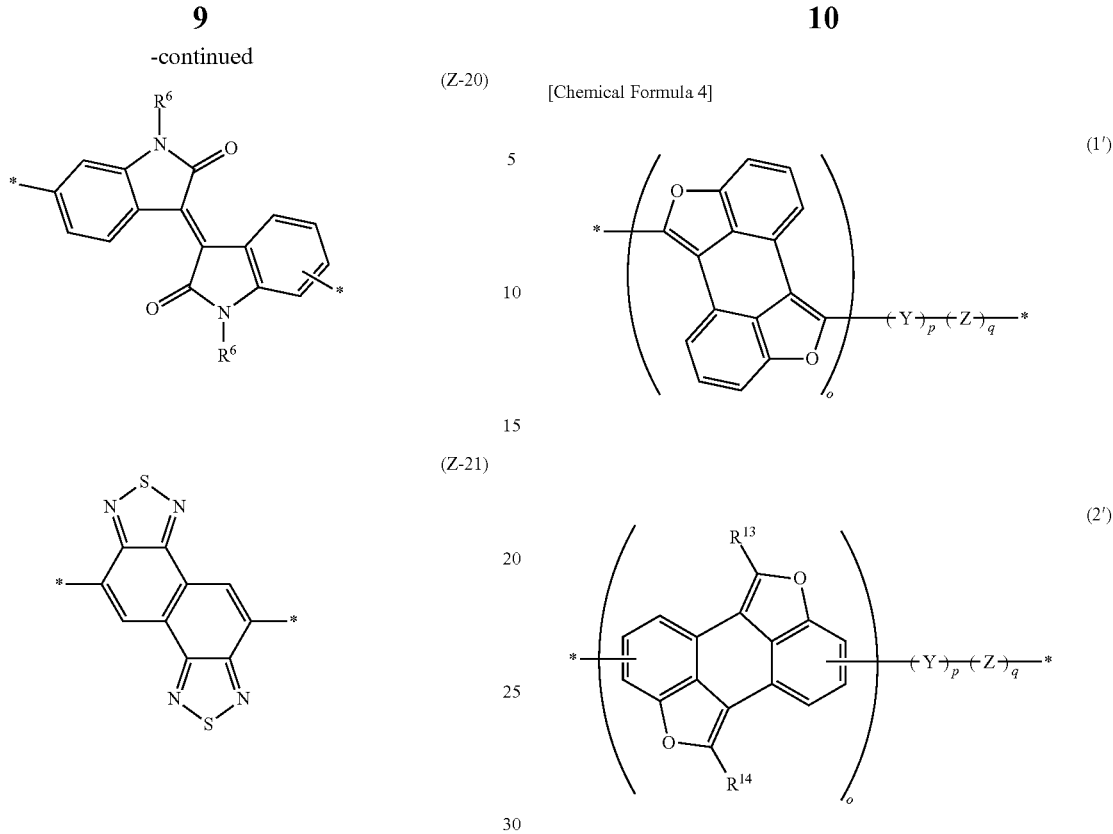

(Z-21)

wherein $X^2$ represents S or $NR^6$, $X^3$ represents S, $NR^6$, $CR^7R^8$, or $SiR^7R^8$, $X^5$ represents S, O, or $NR^6$, $R^6$, $R^7$, and $R^8$ each represent an optionally substituted hydrocarbon group, any hydrogen atom in the constitutional units represented by Group Z may be substituted with a fluorine atom, a chlorine atom, a bromine atom, an iodine atom, a cyano group, a nitro group, a hydroxyl group, a thiol group, an —$NR^9R^{10}$ group, an optionally substituted hydrocarbon group, or an optionally substituted heterocyclic group, $R^9$ and $R^{10}$ each represent an optionally substituted hydrocarbon group.

Examples of the hydrocarbon group with which the hydrogen atoms in the constitutional units represented by Group Y or Group Z are optionally substituted, as well as the optionally substituted hydrocarbon groups represented by $R^3$, $R^6$, $R^7$, and $R^8$ of $NR^3$ represented by $X^1$ and $X^4$ in Group Y, $NR^6$ represented by $X^2$ and $X^5$ in Group Z, and $NR^6$, $CR^7R^8SiR^7R^8$ represented by $X^3$ include the same groups as the optionally substituted hydrocarbon groups represented by $R^{13}$ and $R^{14}$ in the above formula (2).

When the first bibenzo[b]furan compound contains constitutional units of the above Group λ or Group Z, the first bibenzo[b]furan compound is represented by the following general formula (1') or (2'), and the sequence of the o, p, or q units of constitutional unit in the general formula (1') or (2') is not particularly restricted and any sequence will exert the effect of the present invention. Regarding preferred proportions of the respective constitutional units, p or q for the constitutional units in Group Y or Group Z is from 1 to 10 when the proportion of the constitutional units o in formula (1) or (2) is taken as 1. From the viewpoint of high absorption efficiency in a high wavelength region, the value of p is more preferably 0 to 8, still more preferably 1 to 5. From the viewpoint of high absorption efficiency in a high wavelength region, the value of q is more preferably 0 to 2, still more preferably 1 or 2, and particularly preferably 1.

[Chemical Formula 4]

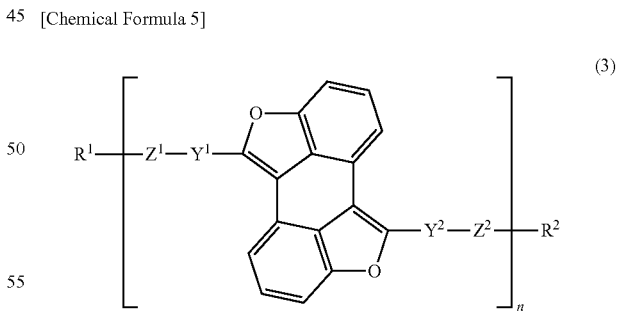

wherein $R^{13}$ and $R^{14}$ each represent the same groups as those of the above formula (2), Y represents a group selected from the above Group Y, Z represents a group selected from the above Group Z, o represents an integer of from 1 to 1000, and p and q each represent an integer of from 0 to 1000.

Preferred examples of the first bibenzo[b]furan compound include compounds represented by the following general formula (3) or (4),

[Chemical Formula 5]

(3)

wherein $R^1$ and $R^2$ each represent a hydrogen atom, a fluorine atom, a chlorine atom, a bromine atom, an iodine atom, an optionally substituted hydrocarbon group, or an optionally substituted heterocyclic group, $Y^1$ and $Y^2$ each represent a single bond or a group formed by linking 1 to 5 types of group selected from among the following (Y-1) to (Y-8) in combination, $Z^1$ and $Z^2$ each represent a single bond or a group selected from among the following (Z-1) to (Z-21), n represents an integer of 1 to 1000,

[Chemical Formula 6]

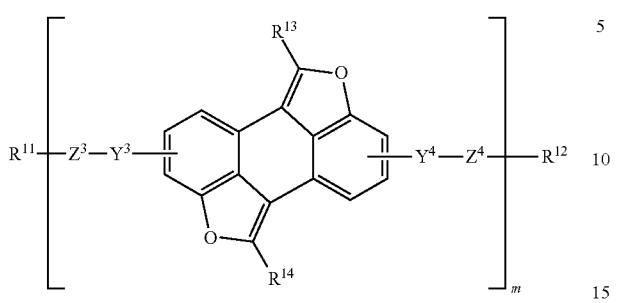

(4)

wherein $R^{11}$, $R^{12}$, or $R^{14}$ represents a hydrogen atom, a fluorine atom, a chlorine atom, a bromine atom, an iodine atom, an optionally substituted hydrocarbon group, or an optionally substituted heterocyclic group, $Y^3$ and $Y^4$ each represent a single bond or a group formed by linking 1 to 5 types of group selected from among the following (Y-1) to (Y-8) in combination, $Z^3$ and $Z^4$ each represent a single bond or a group selected from among the following (Z-1) to (Z-21), and m represents an integer of 1 to 1000,

[Chemical Formula 7]

wherein $X^1$ and $X^4$ each represent S, O, or $NR^3$, k represents an integer of 1 to 4, $R^3$ represents an optionally substituted hydrocarbon group, any hydrogen group in (Y-1) to (Y-4) and (Y-6) to (Y-8) may be substituted with a fluorine group, a chlorine atom, a bromine atom, an iodine atom, a cyano group, a nitro group, a hydroxyl group, a thiol group, an —$NR^4R^5$ group, an optionally substituted hydrocarbon group, or an optionally substituted heterocyclic group, $R^4$ and $R^5$ each represent an optionally substituted hydrocarbon group,

[Chemical Formula 8]

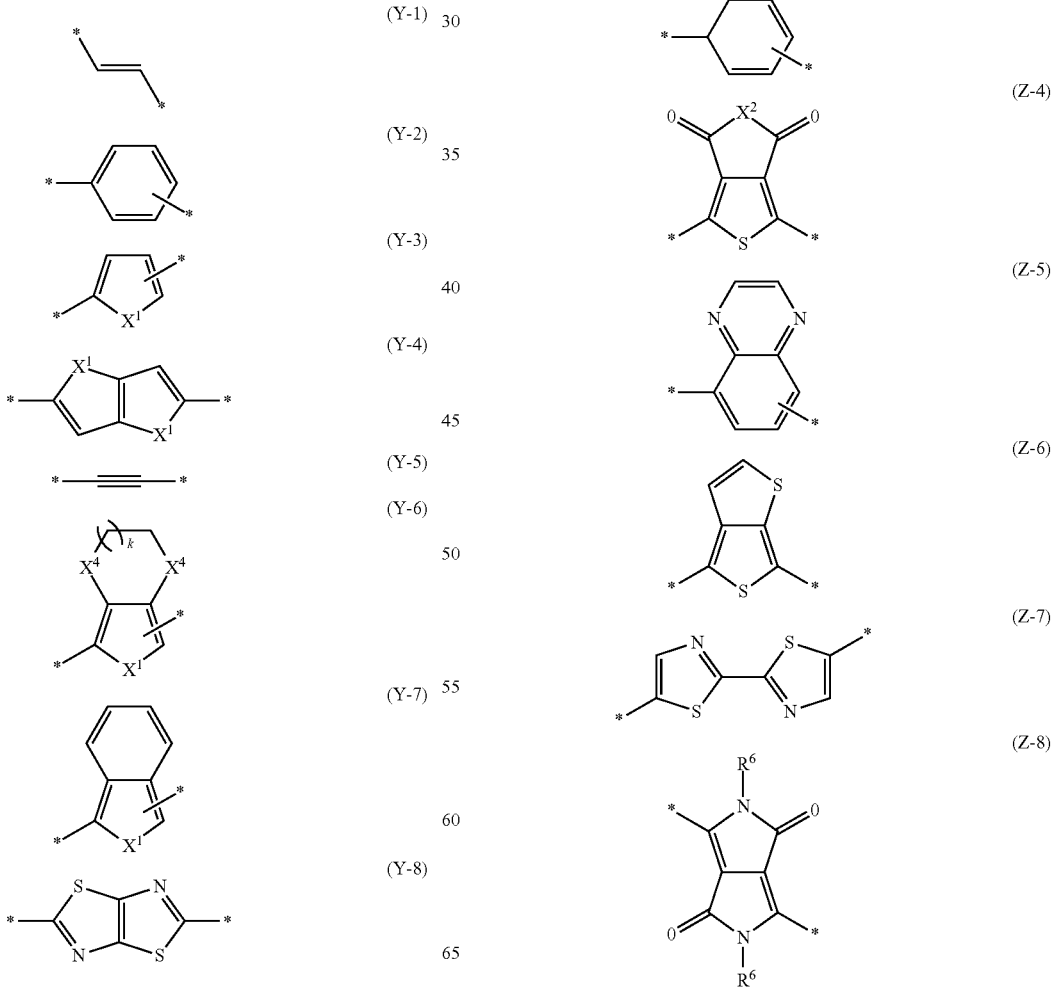

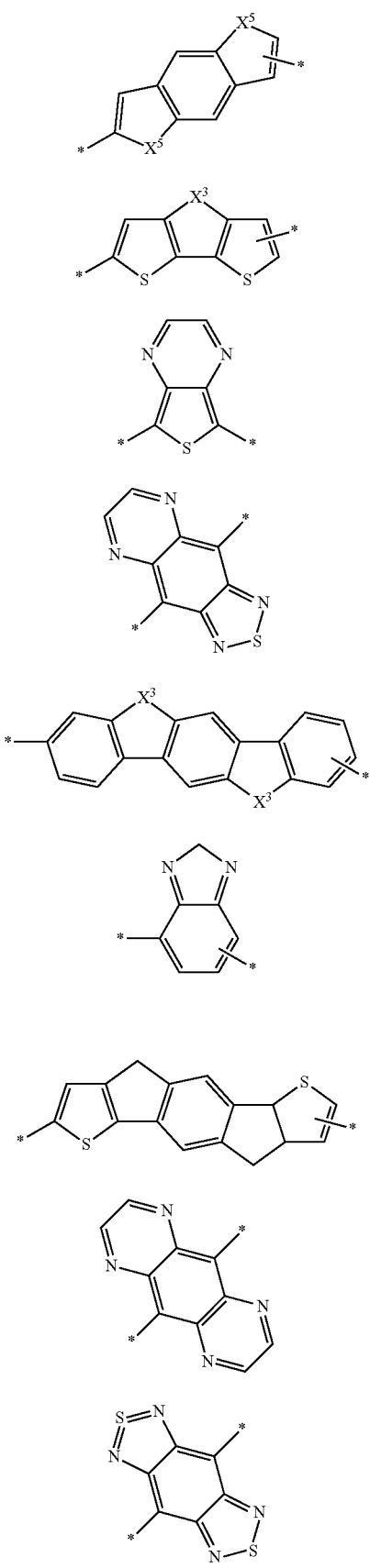
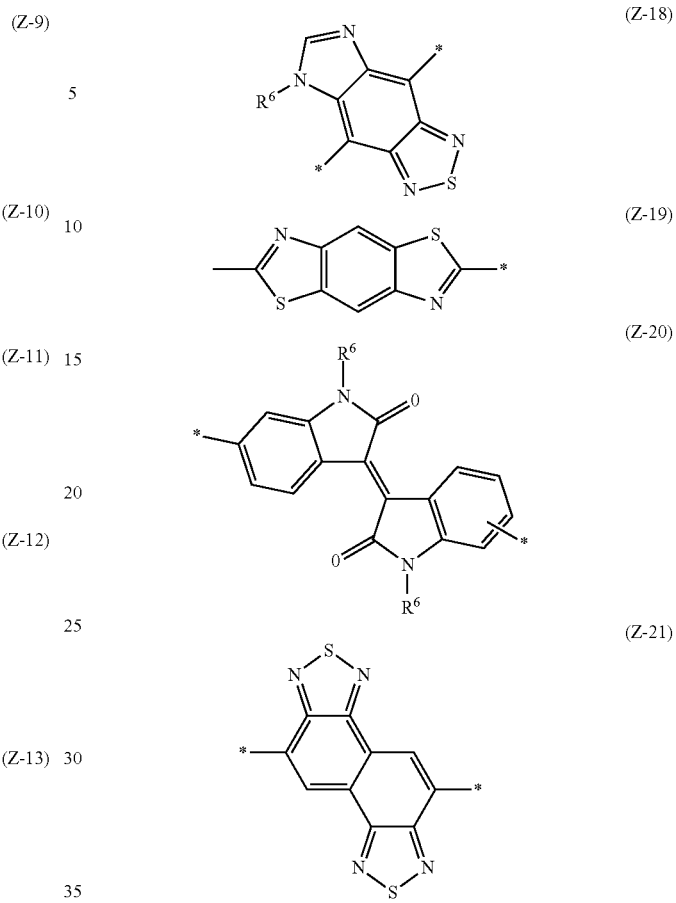

wherein $X^2$ represents S, $NR^6$, or $SiR^7R^8$, $X^3$ represents S, $NR^6$, $CR^7R^8$, or $SiR^7R^8$, $X^5$ represents S, O, or $NR^6$, $R^6$, $R^7$, and $R^8$ each represent an optionally substituted hydrocarbon group, any hydrogen atom in the (Z-1) to (Z-21) groups may be substituted with a fluorine atom, a chlorine atom, a bromine atom, an iodine atom, a cyano group, a nitro group, a hydroxyl group, a thiol group, an —$NR^9R^{10}$ group, an optionally substituted hydrocarbon group, or an optionally substituted heterocyclic group, $R^9$ and $R^{10}$ each represent an optionally substituted hydrocarbon group.

Examples of the optionally substituted hydrocarbon group or the optionally substituted heterocyclic group represented by $R^1$ and $R^2$ in the above general formula (3) and $R^{11}$ and $R^{12}$ in the above general formula (4) include groups the same as those of $R^{13}$ and $R^{14}$ in the above formula (2). Of the groups represented by $R^1$, $R^2$, $R^{11}$, and $R^{12}$, aromatic hydrocarbon groups and aromatic heterocyclic groups are preferred because such compounds can be produced easily and can exert a high photoelectric conversion efficiency.

Of the compounds represented by the above general formula (3), compounds in which at least one of $Y^1$, $Y^2$, or $Z^1$ is not a single bond are preferred because they can be produced easily.

On the other hand, of the compounds represented by the above general formula (4), compounds in which at least one of $Y^3$, $Y^4$, or $Z^2$ is not a single bond are preferred because they can be produced easily.

Specific examples of the first bibenzo[b]furan compound include, but are not restricted to, the following Compound Nos. 1 through 70. $R^1$, $R^2$, and n in the following compounds are the same as those in the above general formula (3), and $R^{11}$, $R^{12}$, and m are the same as those in the above general formula (4).

[Chemical Formula 9]
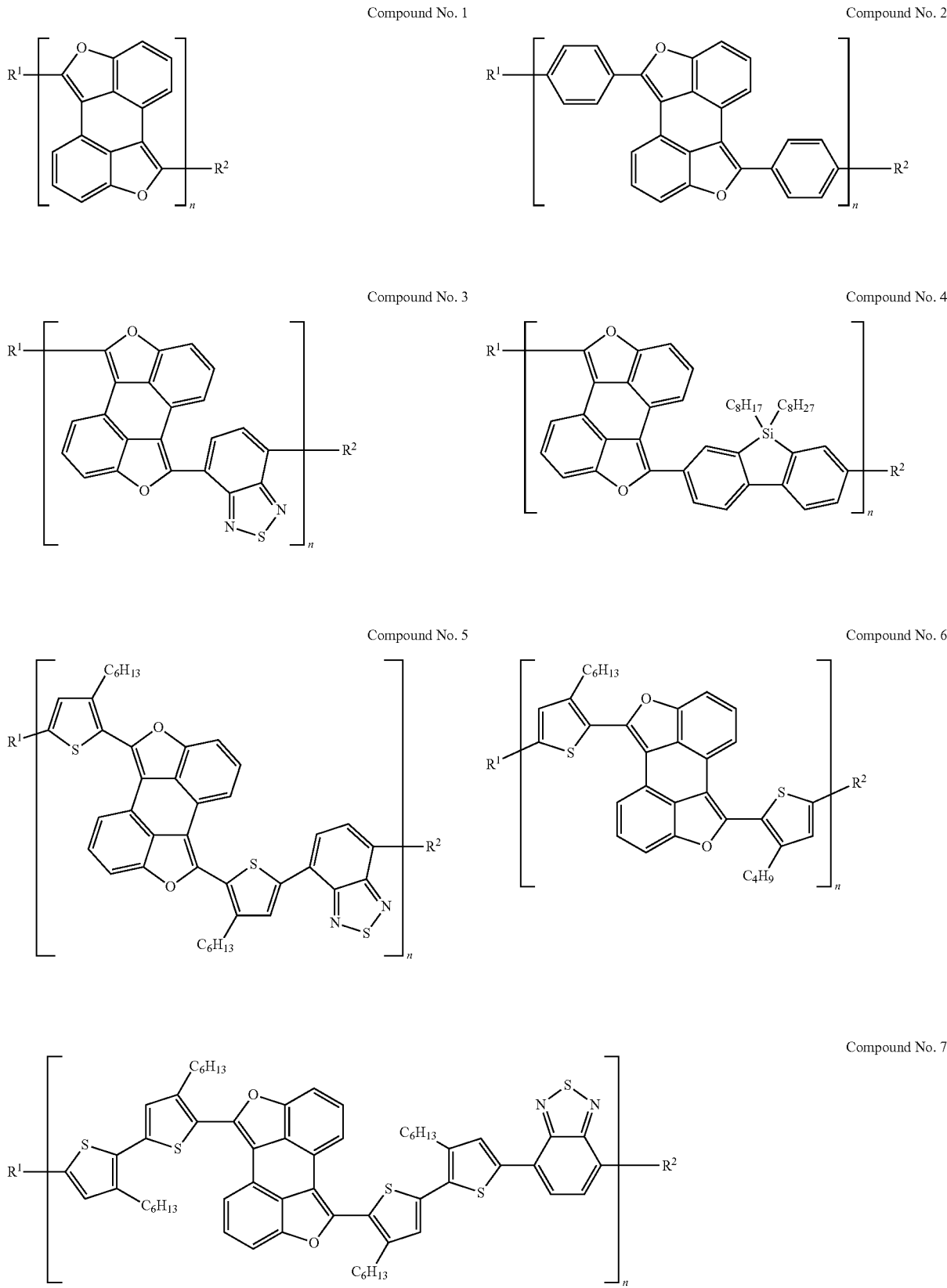

-continued
[Chemical Formula 9A]
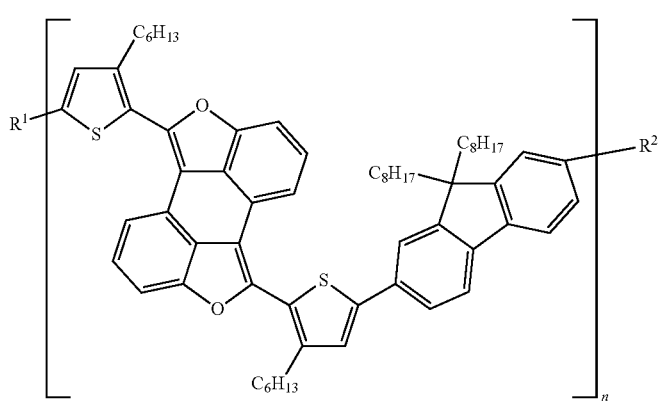
Compound No. 8
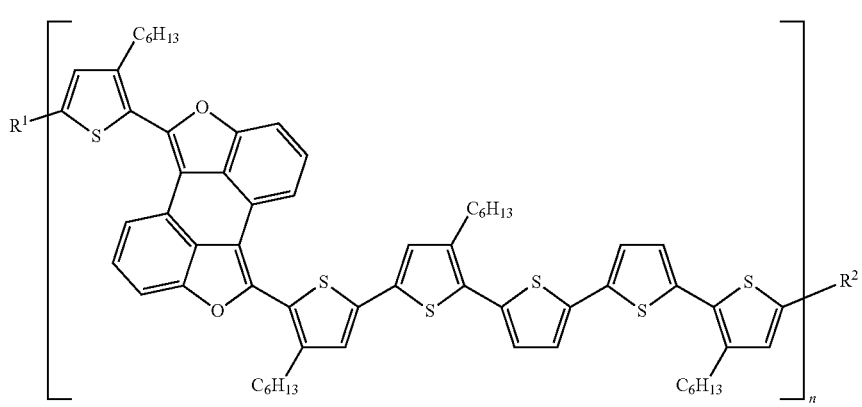
Compound No. 9
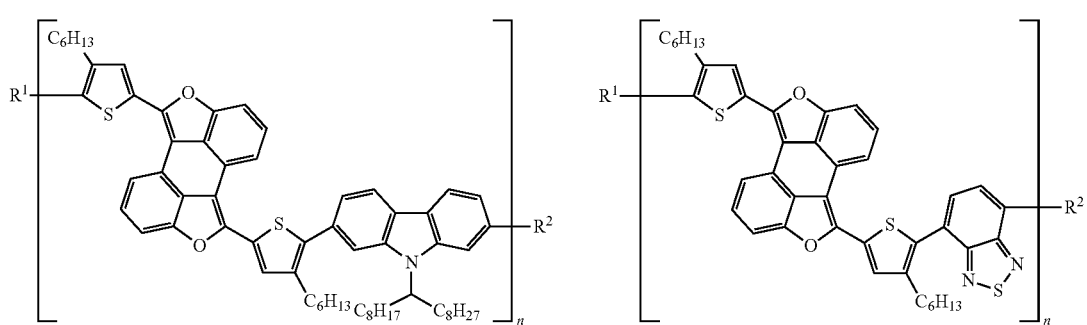
Compound No. 11
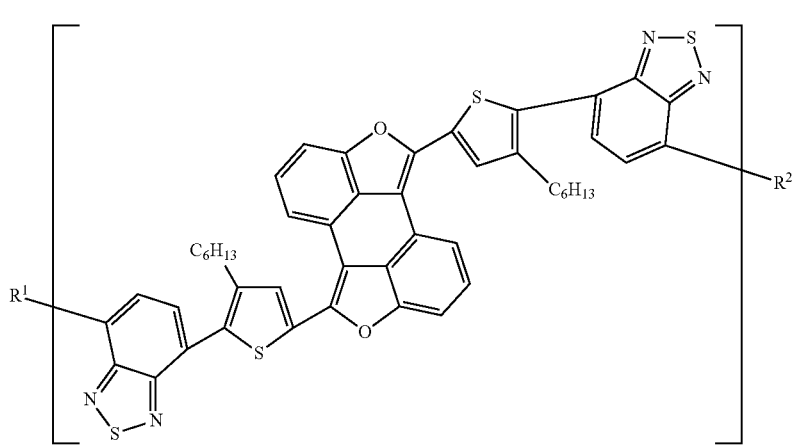
Compound No. 12

-continued
Compound No. 13
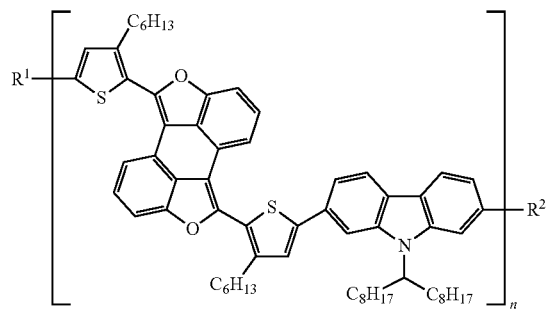
Compound No. 14
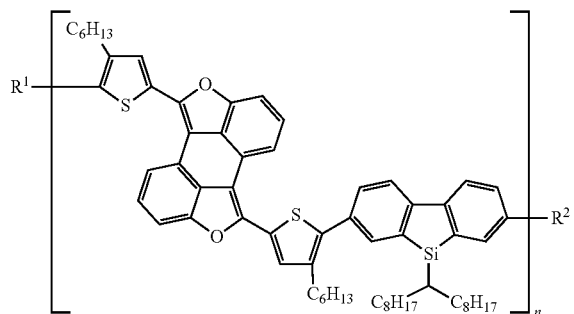
Compound No. 15
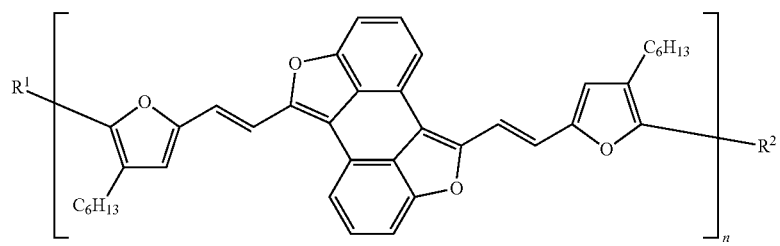
[Chemical Formula 9B]
Compound No. 16
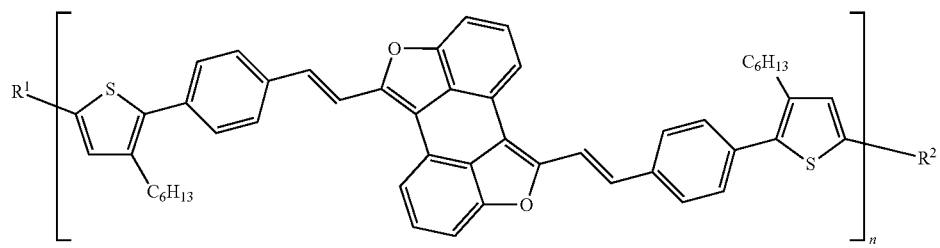
Compound No. 17
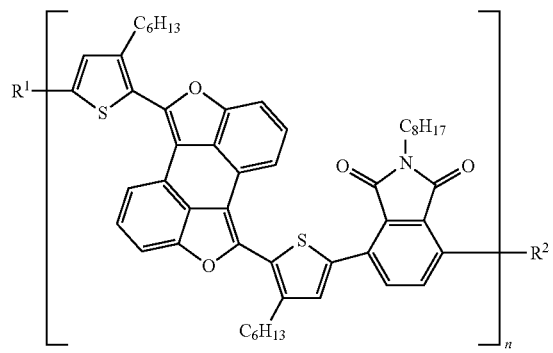
Compound No. 18
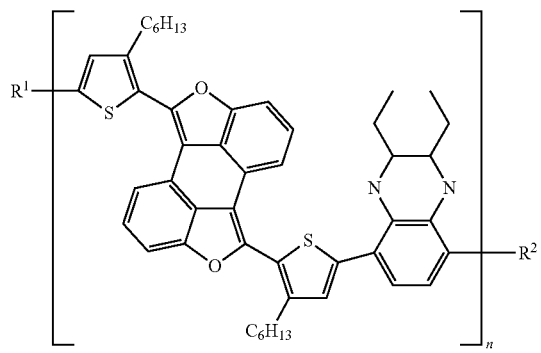
Compound No. 19
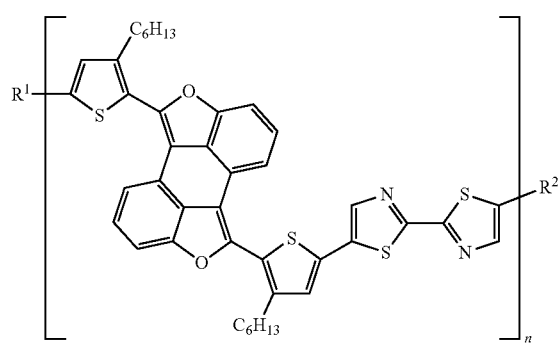
Compound No. 20
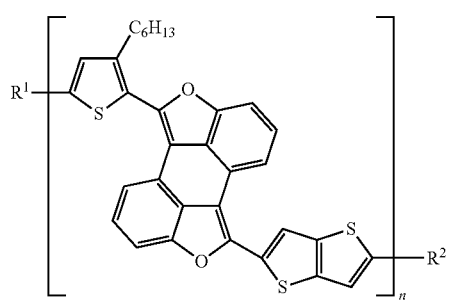

-continued
Compound No. 21
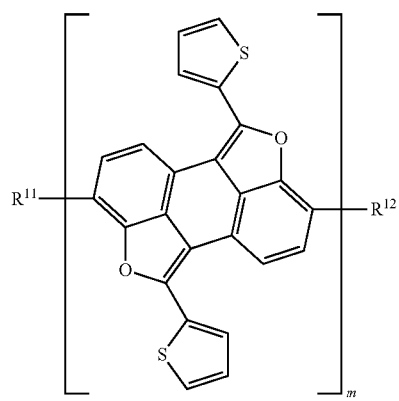
Compound No. 22
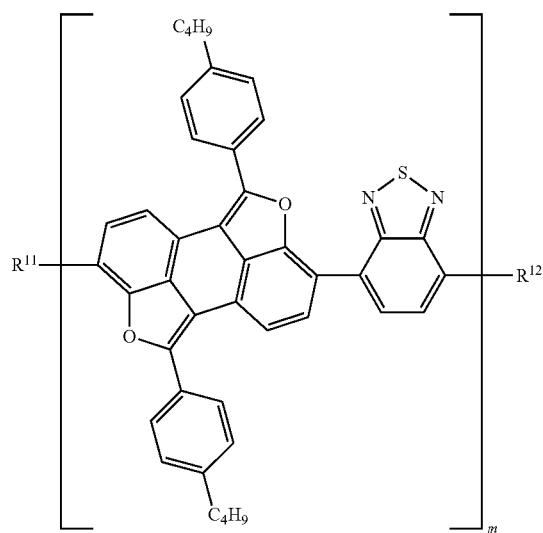
[Chemical Formula 9C]
Compound No. 23
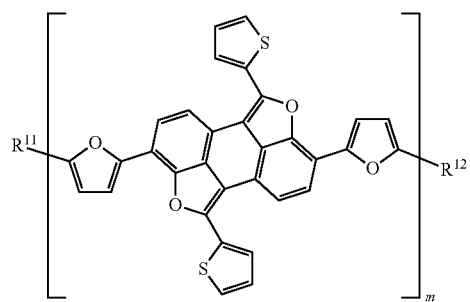
Compound No. 24
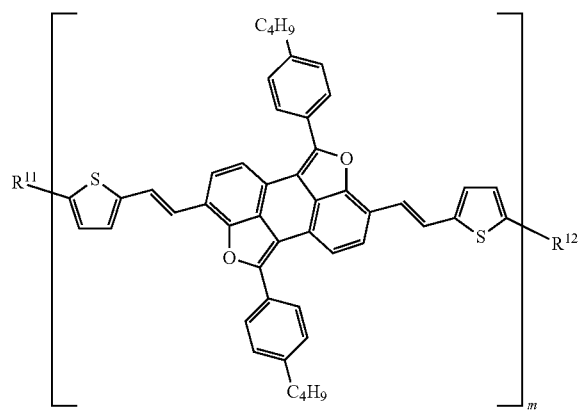
Compound No. 25
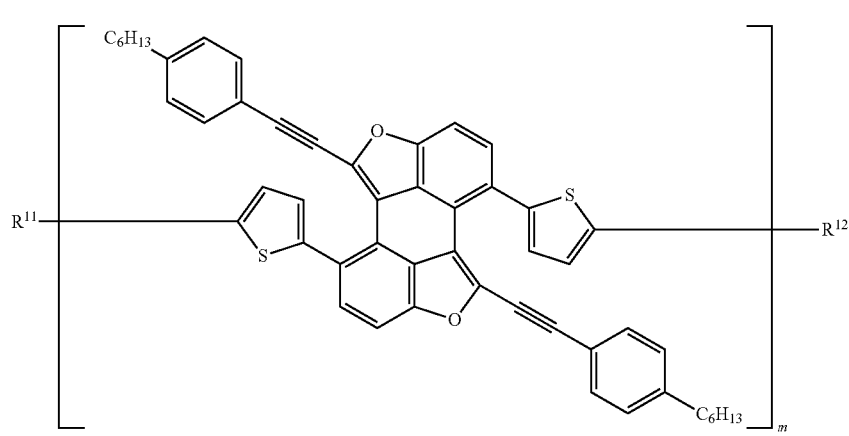

-continued
Compound No. 26
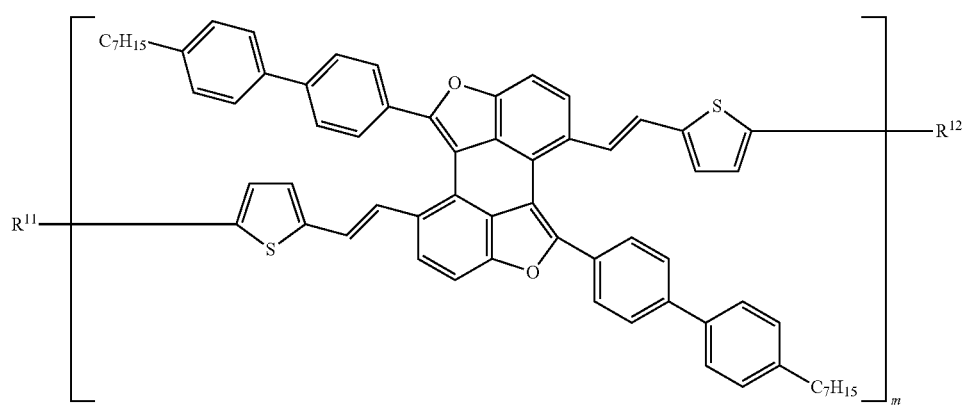
[Chemical Formula 9D]
Compound No. 27
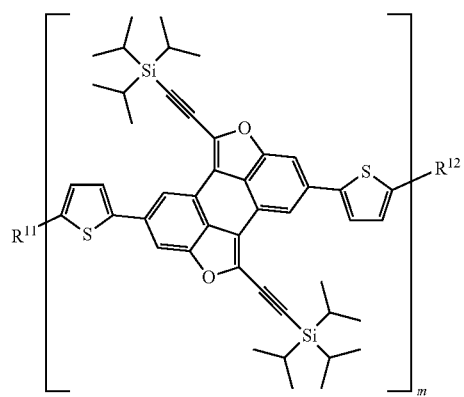
Compound No. 28
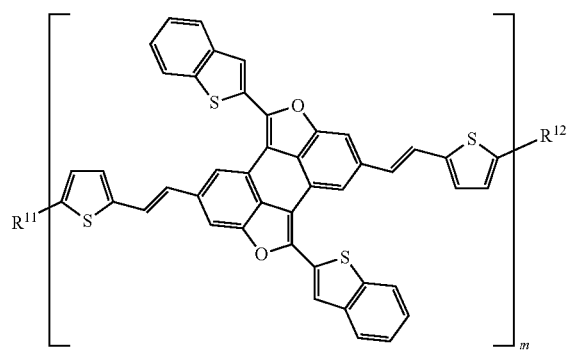
Compound No. 29
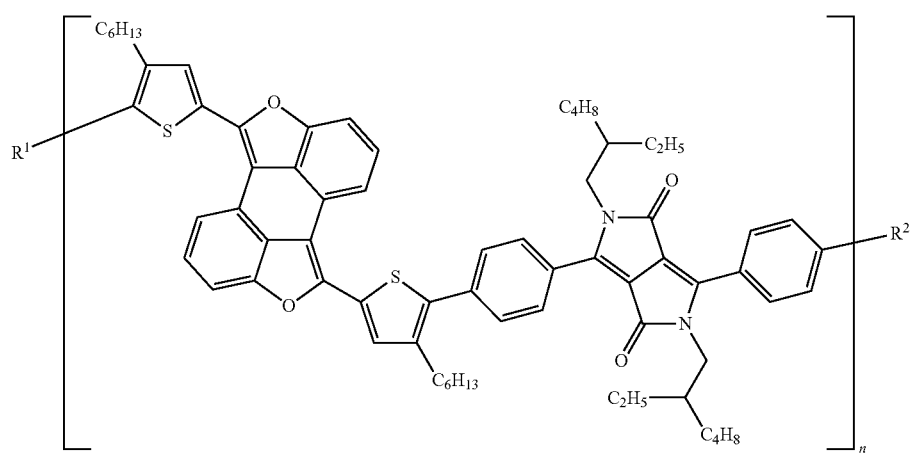

[Chemical Formula 9E]
Compound No. 30
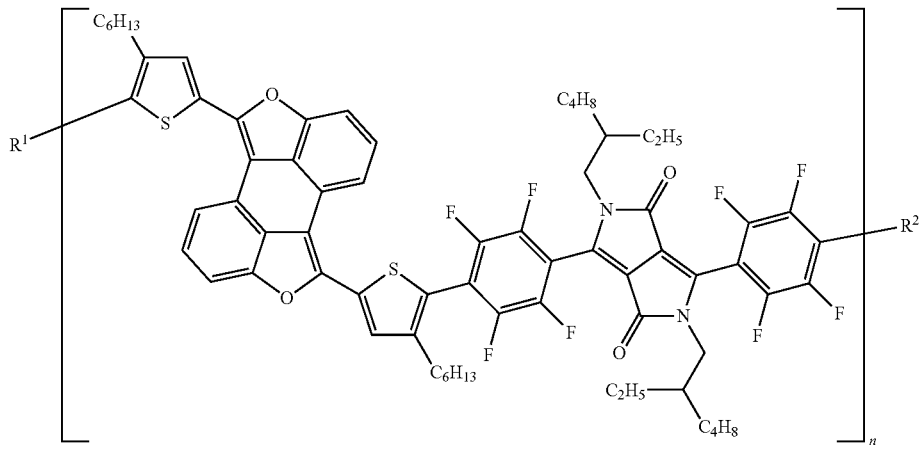
Compound No. 31
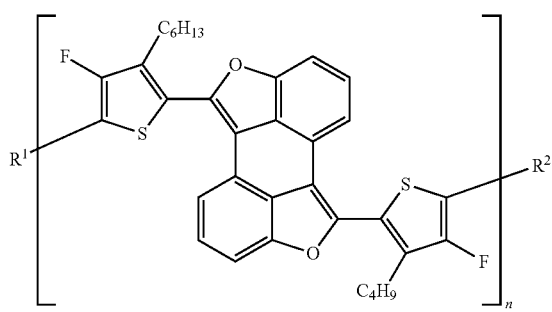
Compound No. 32
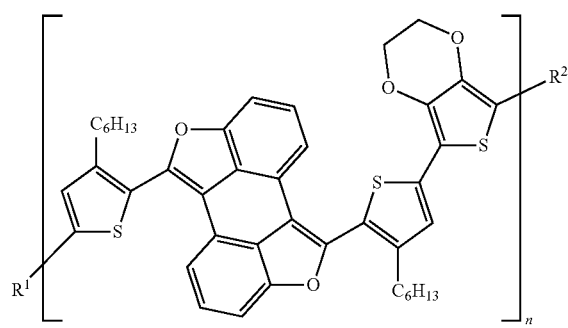
Compound No. 33
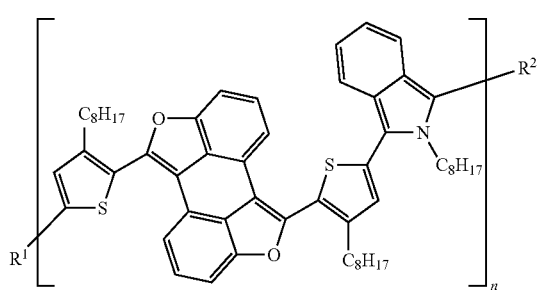
Compound No. 34
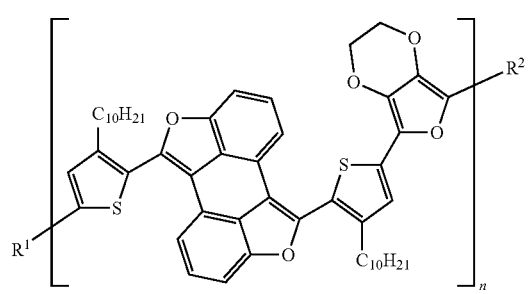
Compound No. 35
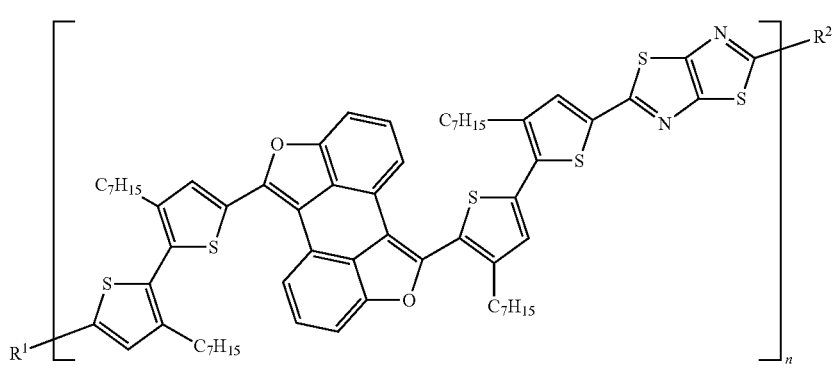

-continued
[Chemical Formula 9F]
Compound No. 36
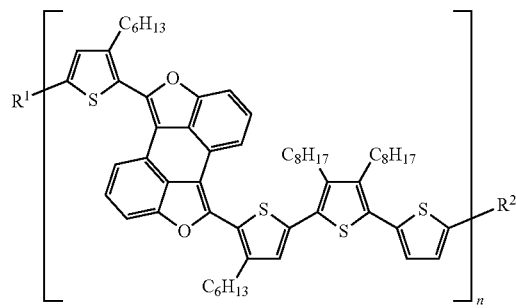
Compound No. 37
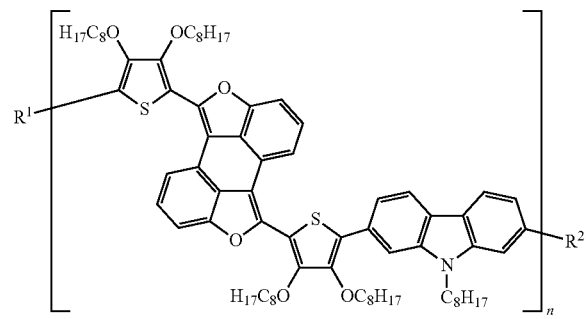
Compound No. 38
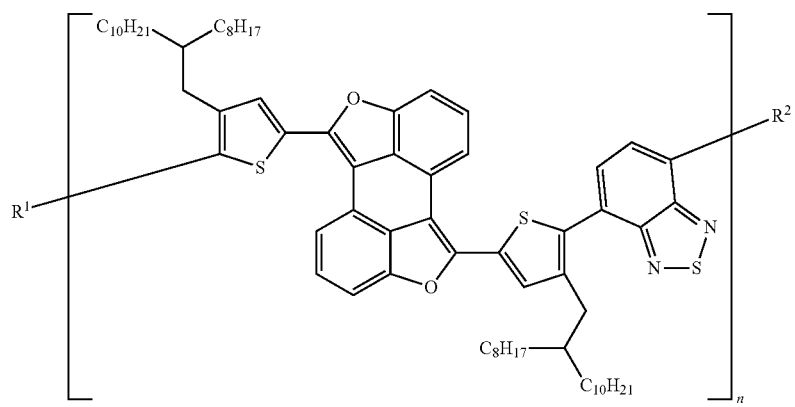
Compound No. 39
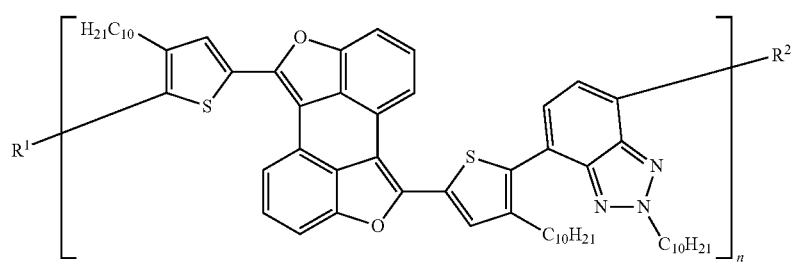
Compound No. 40
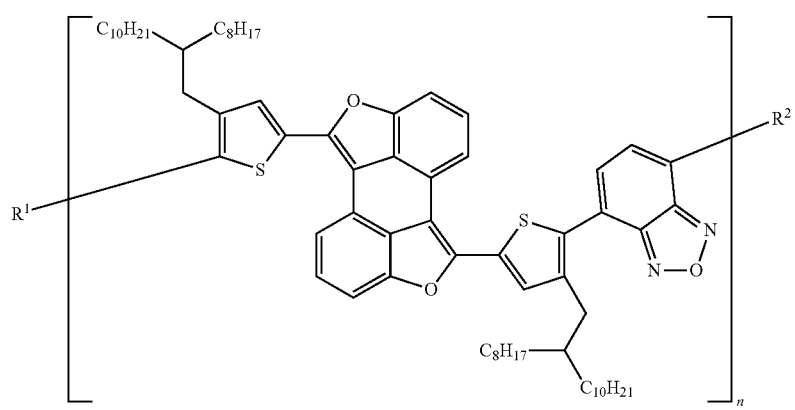

[Chemical Formula 9G]
Compound No. 41
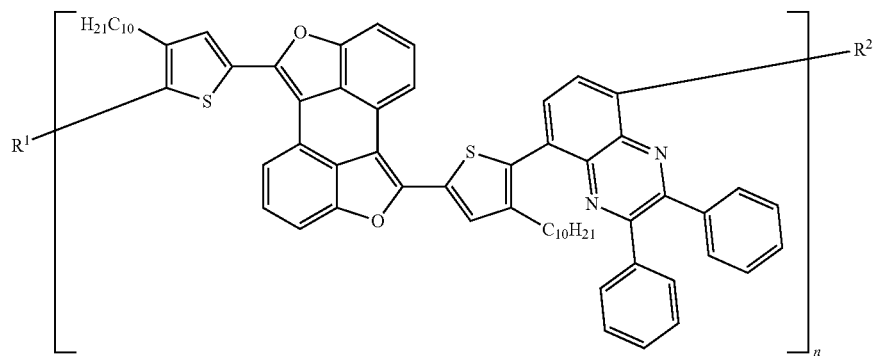
Compound No. 42
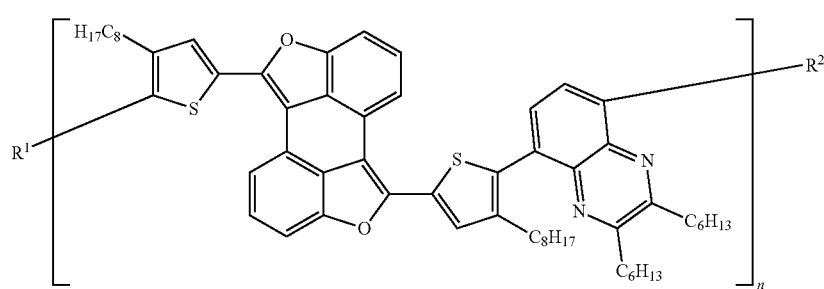
Compound No. 43
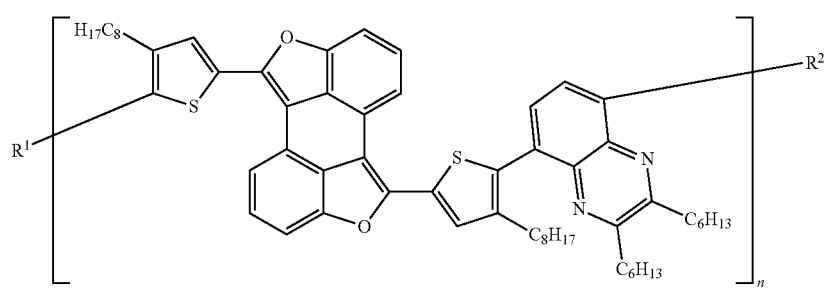
Compound No. 44
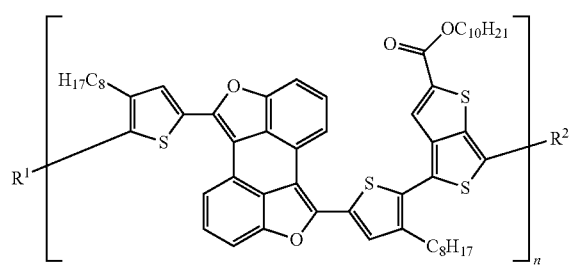
Compound No. 45
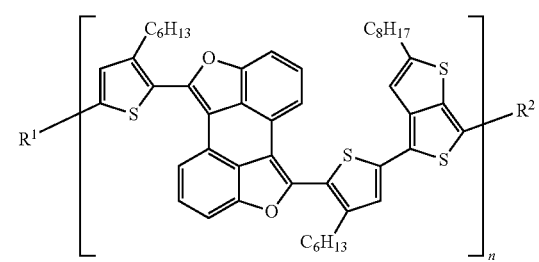
[Chemical Formula 9H]
Compound No. 46
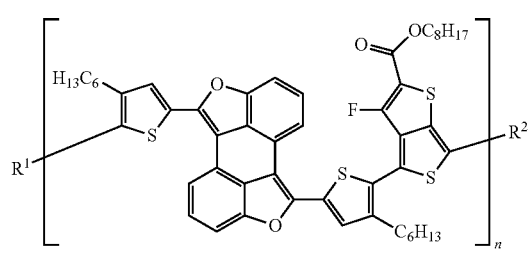
Compound No. 47
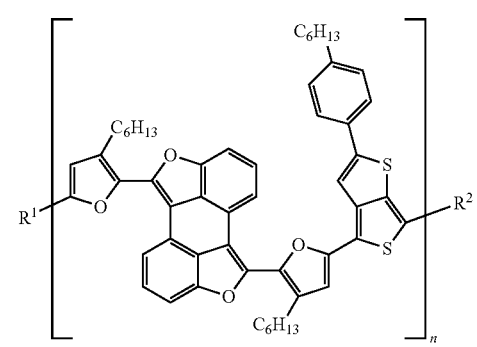

-continued
Compound No. 48
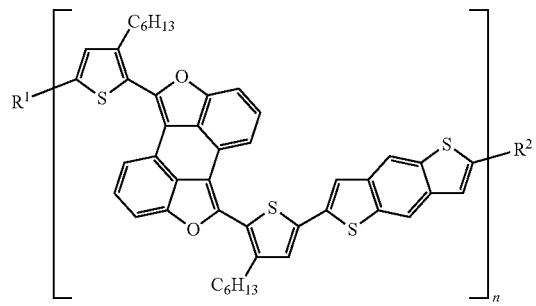
Compound No. 49
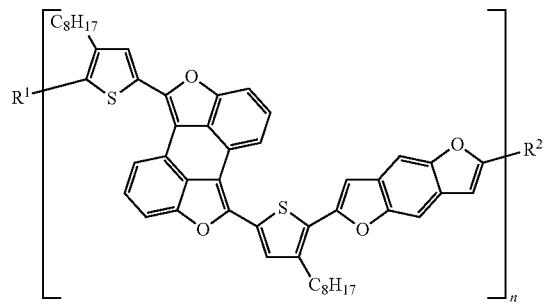
Compound No. 50
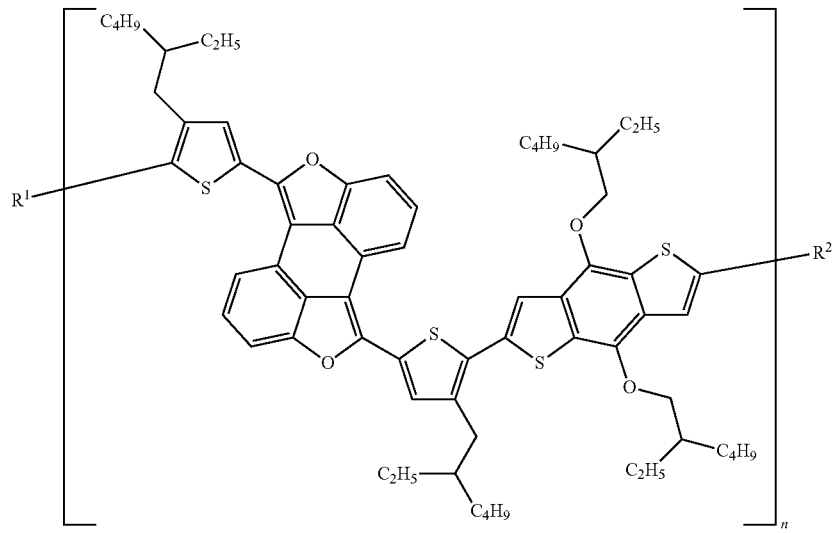
Compound No. 51
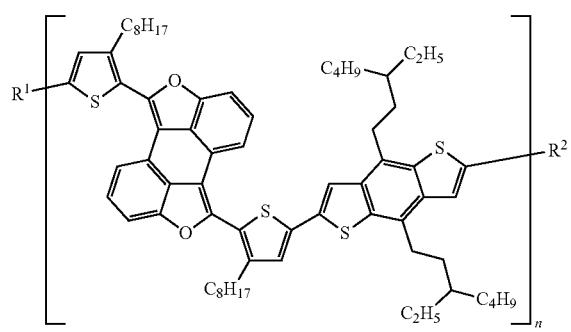
Compound No. 52
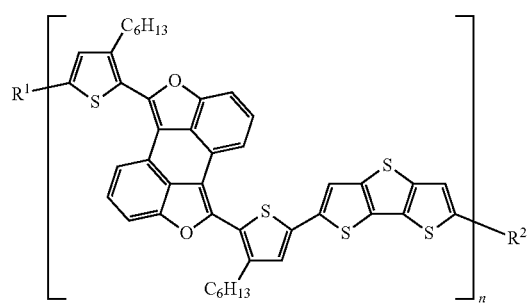
[Chemical Formula 9I]
Compound No. 53
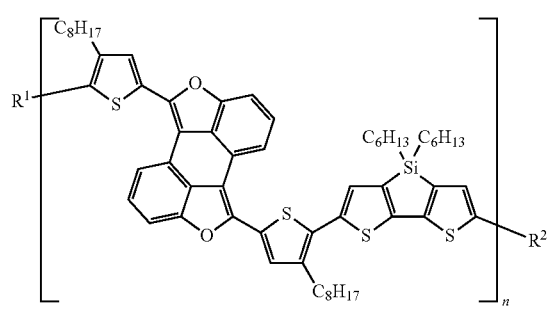
Compound No. 54
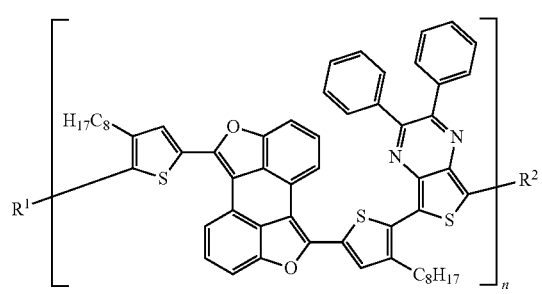

-continued
Compound No. 55
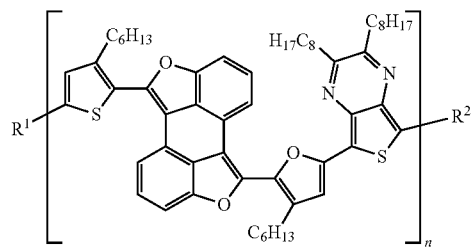
Compound No. 56
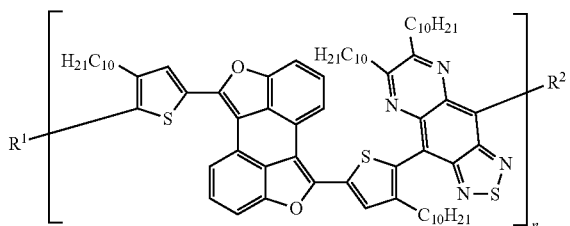
Compound No. 57
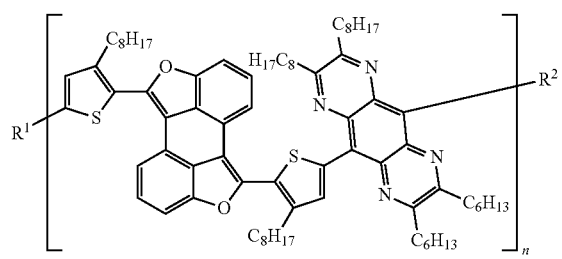
Compound No. 58
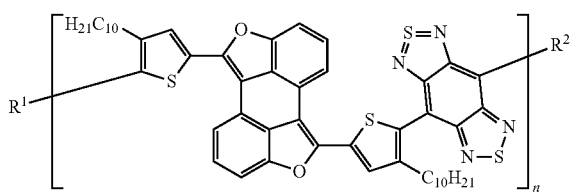
Compound No. 59
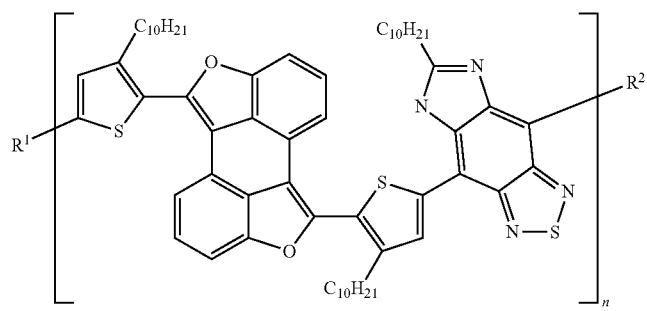
Compound No. 60
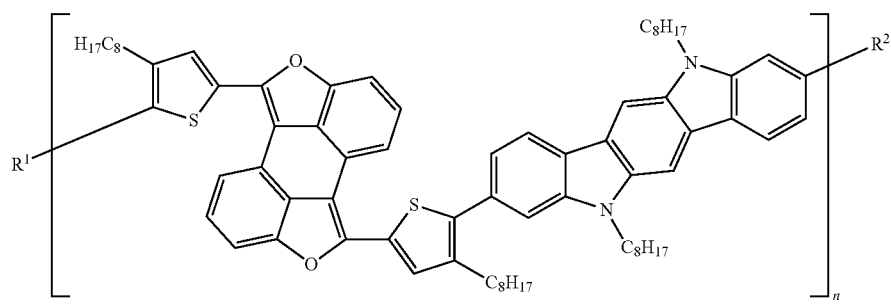
[Chemical Formula 9J]
Compound No. 61
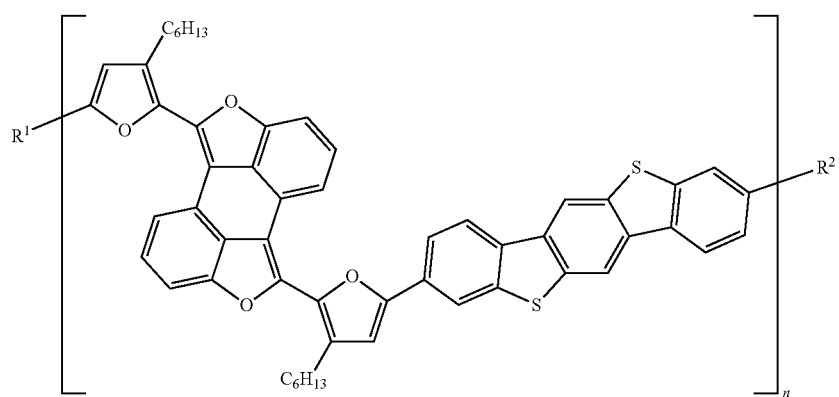

Compound No. 62
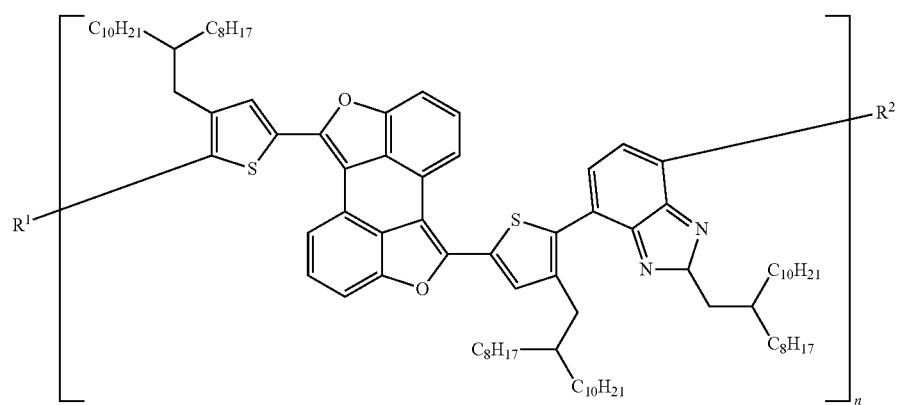
Compound No. 63
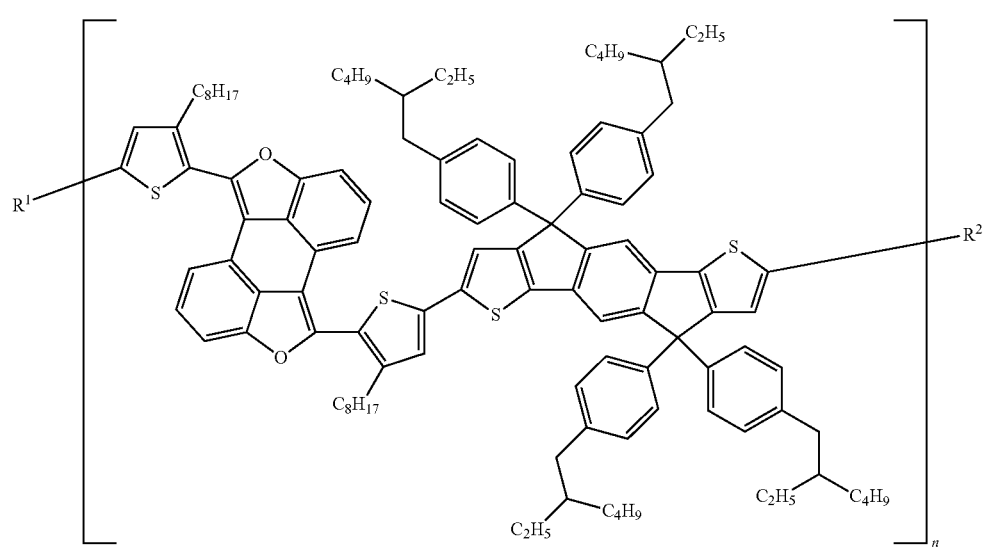
Compound No. 64
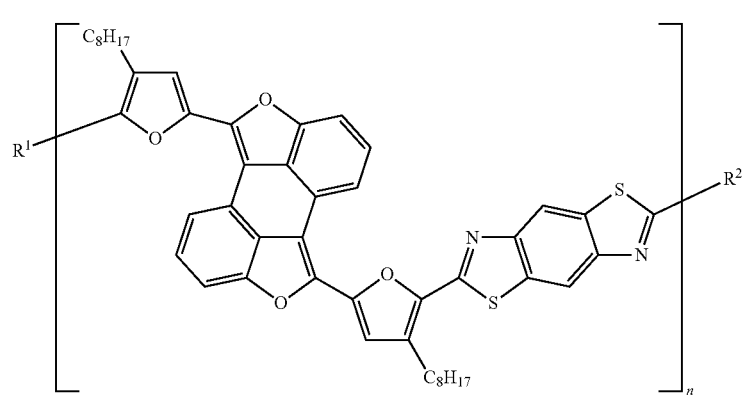

-continued
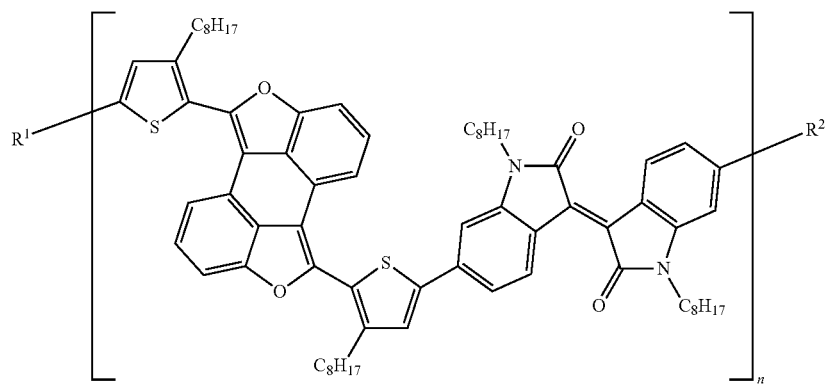
Compound No. 65
[Chemical Formula 9K]
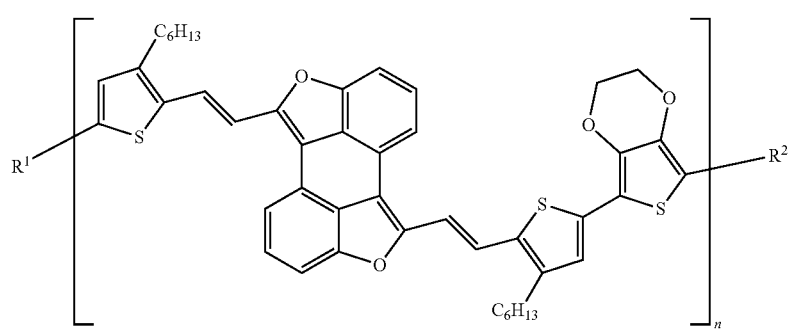
Compound No. 66
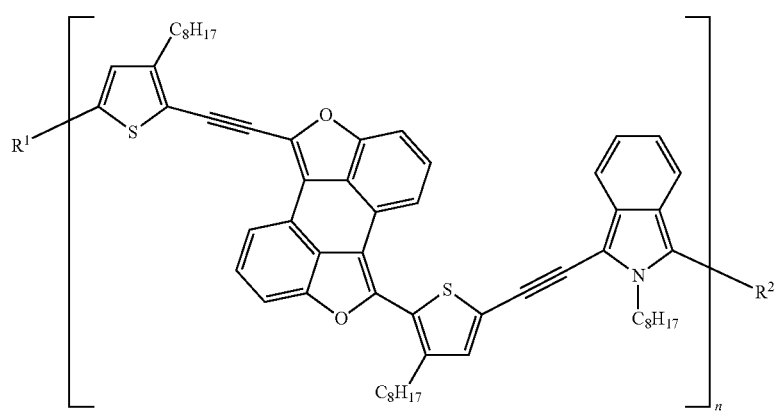
Compound No. 67
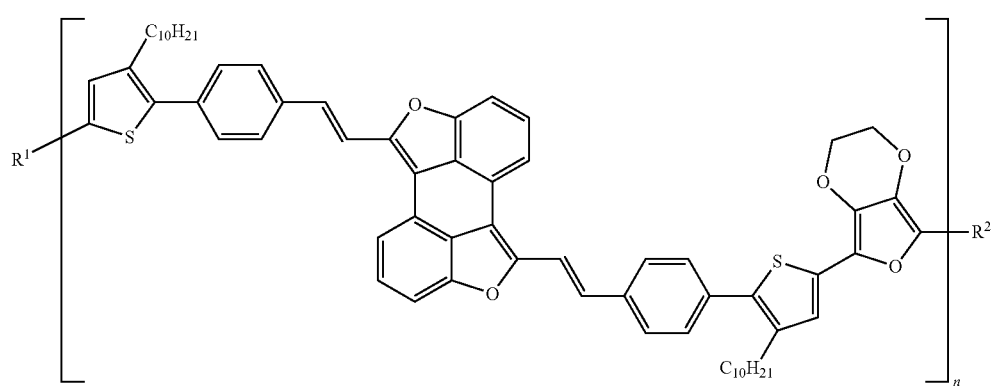
Compound No. 68

Compound No. 69
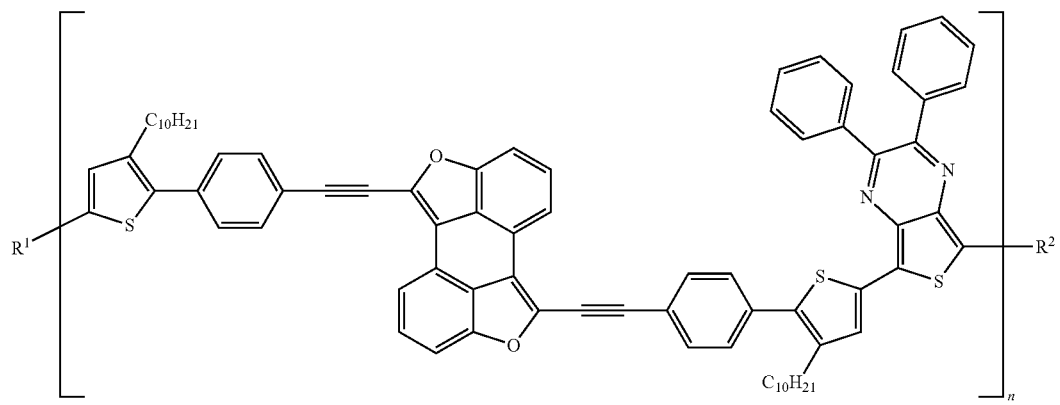
Compound No. 70
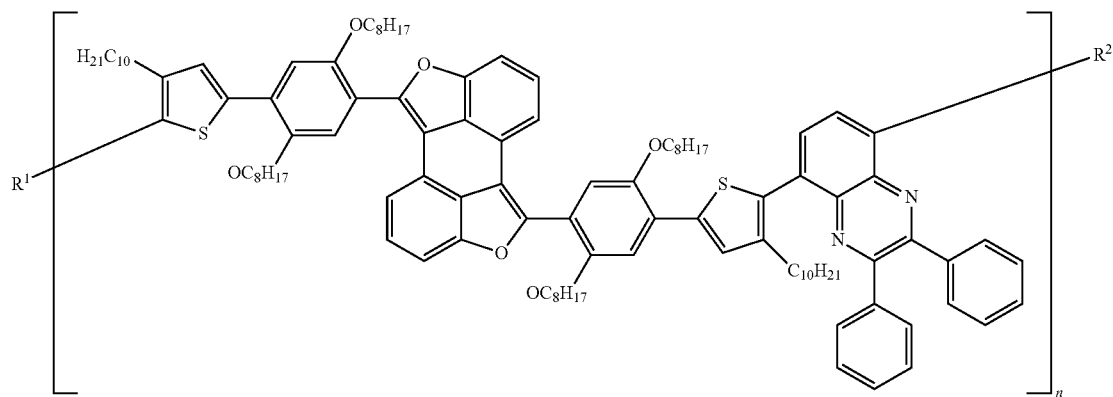
[Chemical Formula 9L]
Compound No. 71
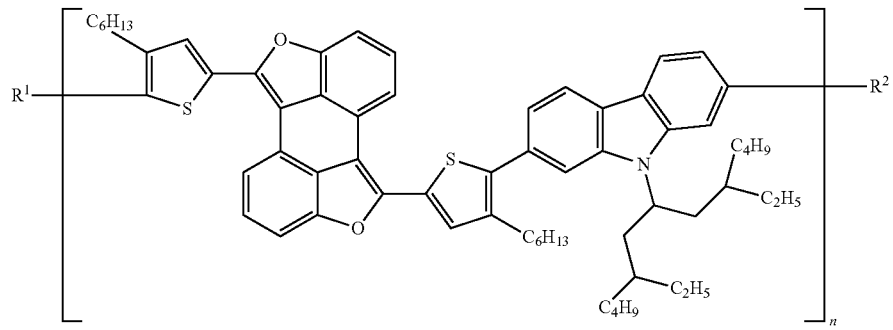
Compound No. 72
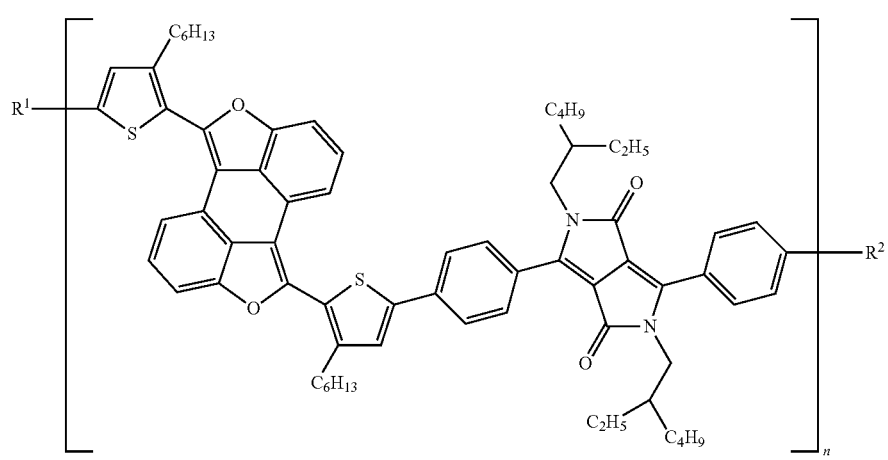

-continued
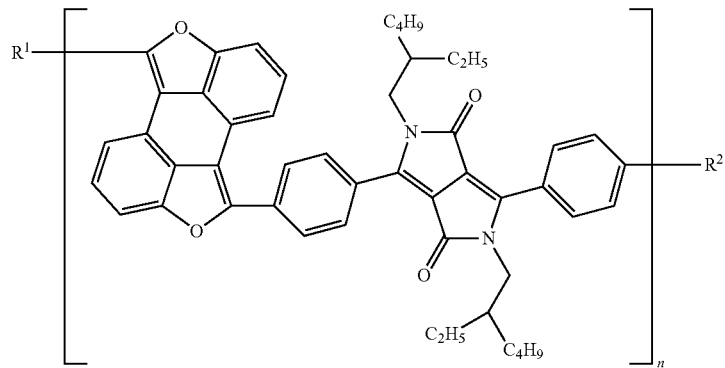
Compound No. 73
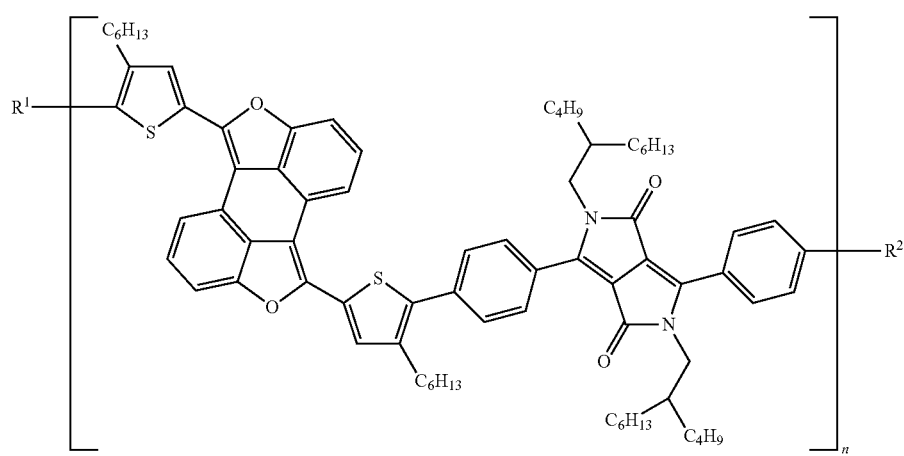
Compound No. 74
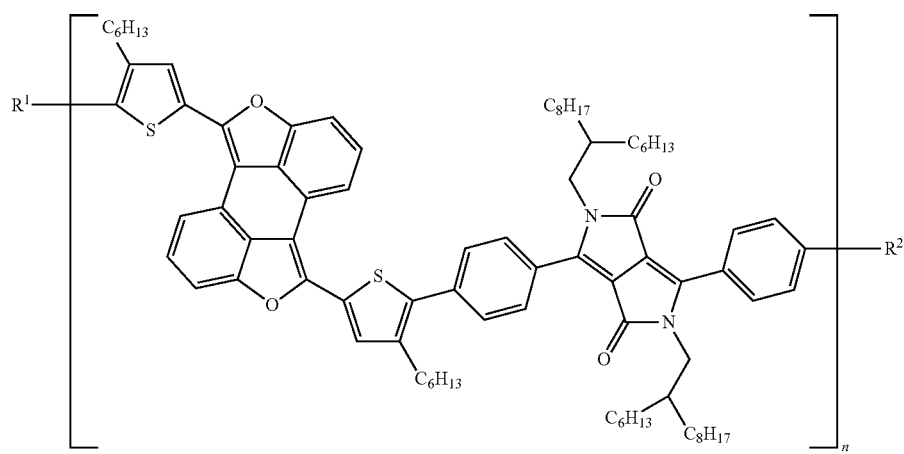
Compound No. 75

[Chemical Formula 9M]
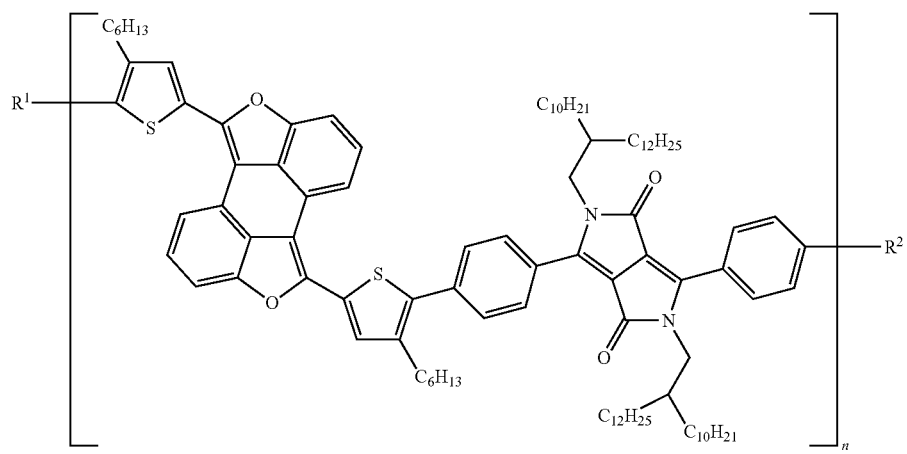
Compound No. 76
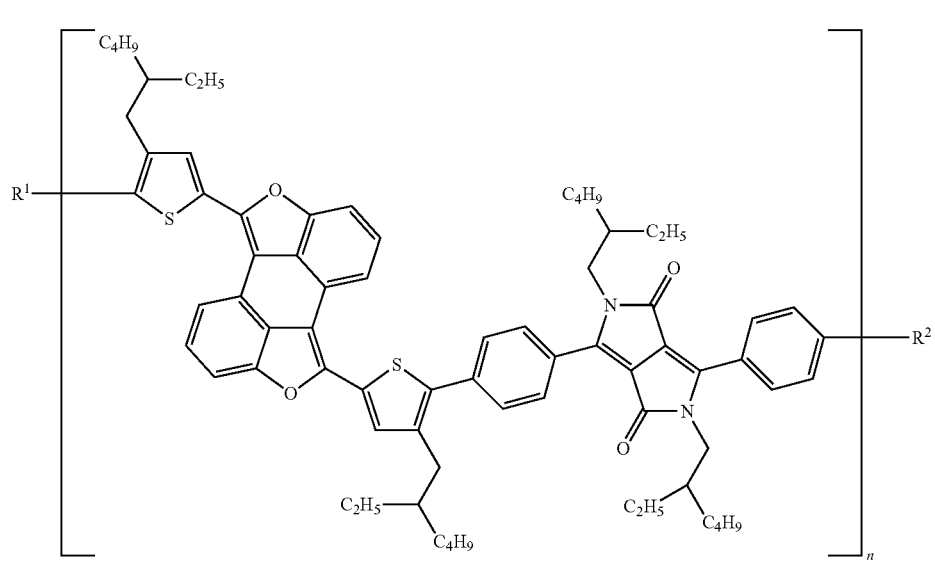
Compound No. 77
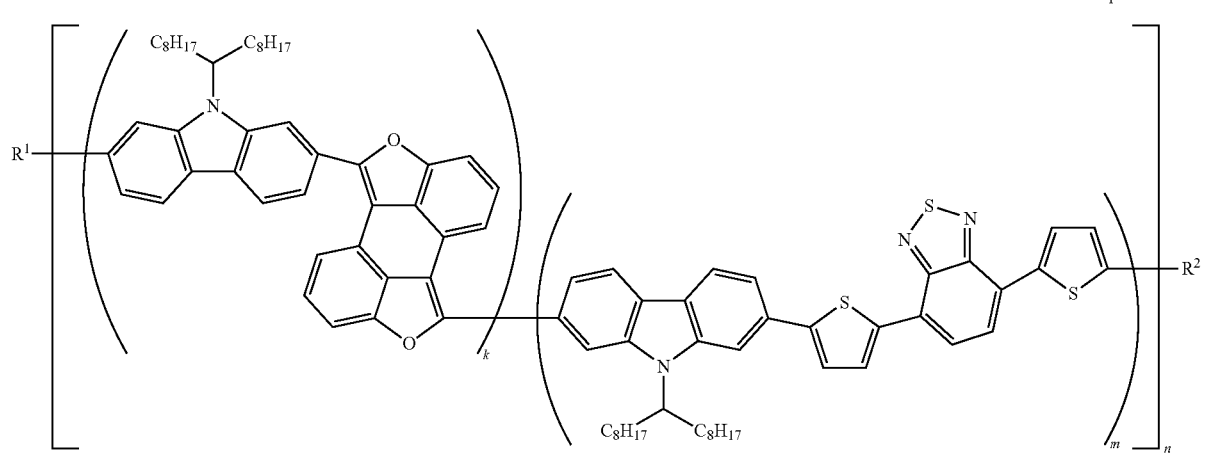
Compound No. 78

None of the first bibenzo[b]furan compounds is limited with respect to the method for the production thereof, and they can be obtained by methods utilizing reactions well-known in the art. The following is one example of the method for producing the bibenzo[b]furan compounds represented by the above general formula (3).

First, a 3,4:3',4'-bibenzo[b]furan skeleton (Compound No. 1 in which n=1, and $R^1$ and $R^2$ are each a hydrogen atom) in a bibenzo[b]furan compound represented by the above general formula (3) is produced via three steps, namely, dietherification, hydrolysis, and cyclization from anthrarufin as shown, for example, in the reaction route provided below.

(Reaction route)

[Chemical Formula 10]

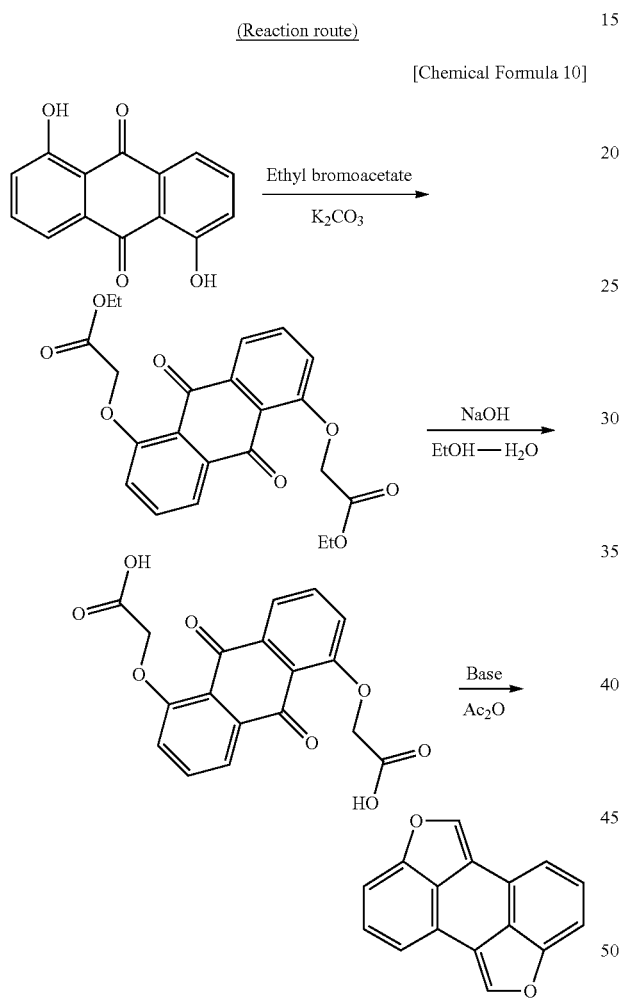

[Chemical Formula 10A]

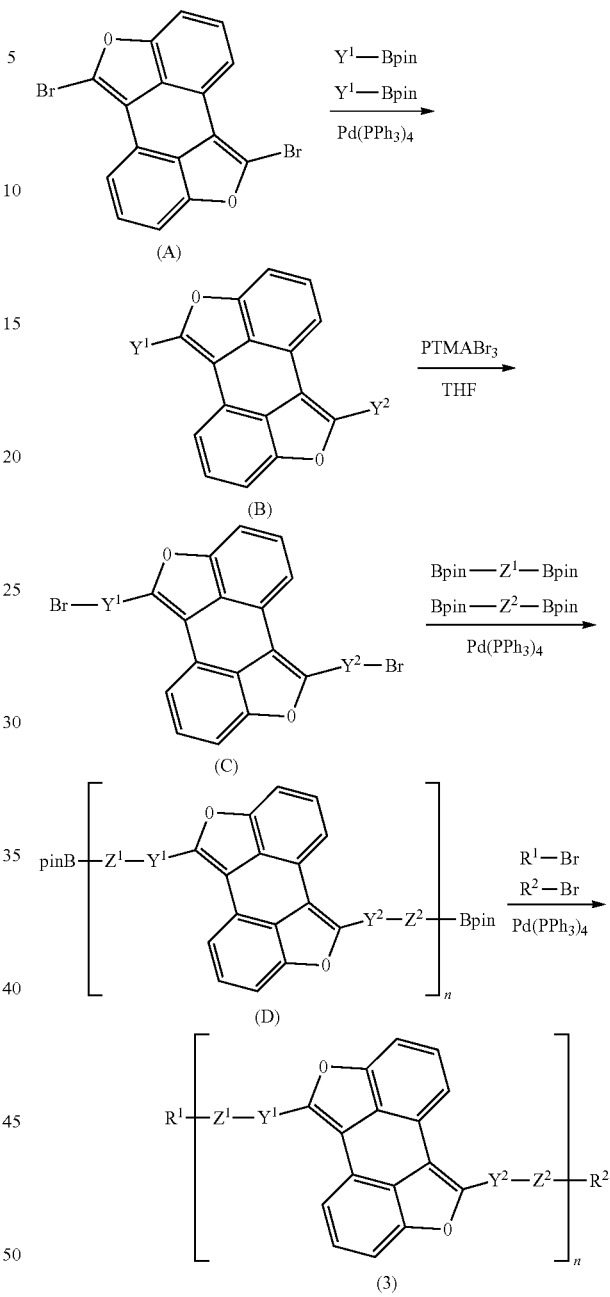

Next, the resulting 3,4:3',4'-bibenzo[b]furan is brominated into dibromobibenzo[b]furan (A).

Subsequently, the dibromobibenzo[b]furan (A) is coupled with corresponding boronic acid pinacol ester derivatives having $Y^1$— or $Y^2$— to form an intermediate (B), which is then brominated with trimethylphenylammonium bromide to form an intermediate (C), which is then converted to a higher molecular weight with corresponding bisboronic acid pinacol ester derivatives having $Z^1$— or $Z^2$—, thereby forming an intermediate (D), which is then capped at terminals thereof, so that a compound represented by the above general formula (3) can be obtained. When quenching is carried out after the formation of the intermediate (D), $R^1$ and $R^2$ are converted into hydrogen atoms.

wherein $R^1$, $R^2$, $Y^1$, $Y^2$, $Z^1$, $Z^2$, and n are the same as those in the above general formula (3).

In the above reaction formula, when the intermediate (C) is used excessively in the reaction between the intermediate (C) and the bisboronic acid pinacol ester derivatives, a bromine-substituted form (D') shown below is also expected to be formed. Both the case where the bromine-substituted form (D') remains as it is and the case where the bromine-substituted form (D') is further reacted with boronic acid pinacol ester derivatives to form a compound (3') described below are permitted without any limitations because both the cases will exert the same effects in the present invention.

In carrying out the various coupling reactions in the above reaction formula, regarding the functional groups bound in the intermediates (A), (B), and (C), it is also allowed to use bibenzofuran derivatives converted into a halogen compound, a triflate form, a boron compound, a silicon compound, a zinc compound, or a tin compound corresponding thereto besides bromine. Corresponding to the above-mentioned intermediates, in $R^1$—Br, $R^2$—Br, Bpin-$Z^1$-Bpin, and Bpin-$Z^2$-Bpin, even in the case that desired bibenzofuran derivatives are synthesized using intermediates converted into a halogen compound, a triflate form, a boron compound, a silicon compound, a zinc compound, or a tin compound corresponding thereto corresponding to the intermediates (A), (B), and (C) to be used, no particular limitations are made because the same effects will be exerted thereby for the present invention.

[Chemical Formula 11]

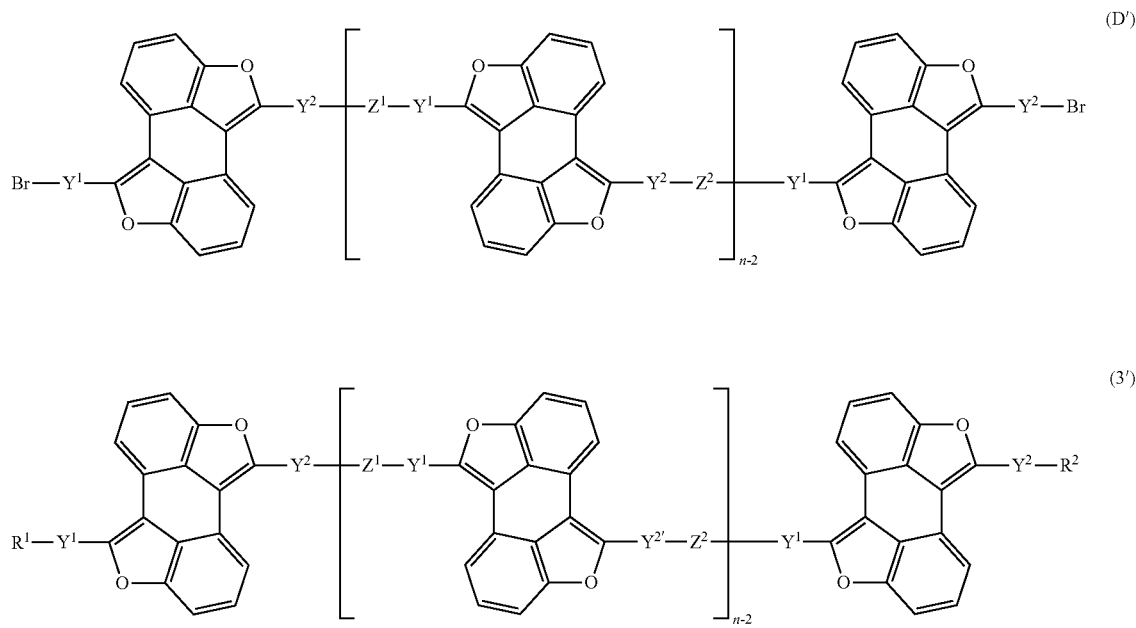

wherein $R^1$, $R^2$, $Y^1$, $Y^2$, $Z^1$, $Z^2$, and n are the same as those in the above general formula (3).

The bibenzo[b]furan compound of the present invention is suitable as an organic semiconductive material and also can be used for applications such as antioxidants.

<Photoelectric Conversion Material>

The photoelectric conversion material of the present invention comprises (A) a p-type organic semiconductive material comprising at least one first bibenzo[b]furan compound and (B) an n-type organic semiconductive material.

The p-type organic semiconductive material (A) should just contain at least one first bibenzo[b]furan compound, which may be used together with other known materials. Examples thereof include phthalocyanine-based pigments, indigo-based or thioindigo-based pigments, quinacridone-based pigments, triarylmethane derivatives, triarylamine derivatives, oxazole derivatives, hydrazone derivatives, stilbene derivatives, pyrazoline derivatives, polysilane derivatives, polyphenylenevinylene and derivatives thereof (e.g., poly[2-methoxy-5-(2-ethylhexyloxy)-1,4-phenylenevinylene]: MEH-PPV, and poly[2-methoxy-5-(3',7'-dimethyloctyloxy)-1,4-phenylenevinylene]), polythiophene and derivatives thereof (e.g., poly(3-dodecylthiophene), poly(3-hexylthiophene):P3HT, and poly(3-octylthiophene)), and poly-N-vinylcarbazole derivatives.

In the case of using other known materials as the p-type organic semiconductive material (A), the content of the first bibenzo[b]furan compound in the p-type organic semiconductive material (A) is preferably 1 to 99% by weight, more preferably 1 to 80% by weight.

As the n-type organic semiconductive material (B), perylene-based pigments, perynone-based pigments, polycyclic quinone-based pigments, azo pigments, C60 fullerene and C70 fullerene as well as derivatives thereof, etc. can be used. Moreover, organic metal complexes [e.g., tris(8-quinolato)aluminum, bis(10-benzo[h]quinolato)beryllium, beryllium salt of 5-hydroxyflavone, and aluminum salt of 5-hydroxyflavone], oxadiazole derivatives [e.g., 1,3-bis[(5'-(p-tert-buthylphenyl)-1,3,4-oxadiazol-2'-yl)]benzene], triazole derivatives [e.g., 3-(4'-tert-buthylphenyl)-4-phenyl-5-(4"-biphenyl)-1,2,4-triazole], phenanthroline derivatives [e.g., 2,9-dimethyl-4,7-diphenyl-1,10-phenanthroline (bathocuproine, BCP)], triazine derivatives, quinoline derivatives, quinoxaline derivatives, diphenylquinone derivatives, nitro-substituted fluorenone derivatives, thiopyran dioxide derivatives, etc. also can be used. Of the n-type organic semiconductive materials (B), C60 fullerene and C70 fullerene as well as derivatives thereof are preferred because of having a high carrier mobility as n-type materials and/or being high in charge separation efficiency. The compounds as examples of n-type organic semiconductive materials each may be used singly or a plurality of them may be used in combination.

Examples of C60 fullerene, C70 fullerene, and derivatives thereof include the C1 to C6 compounds provided below, and of these, PCBM (phenyl-C61-butyric acid methyl ester) because of their good consistency of electron level and their easy availability.

[Chemical Formula 12]

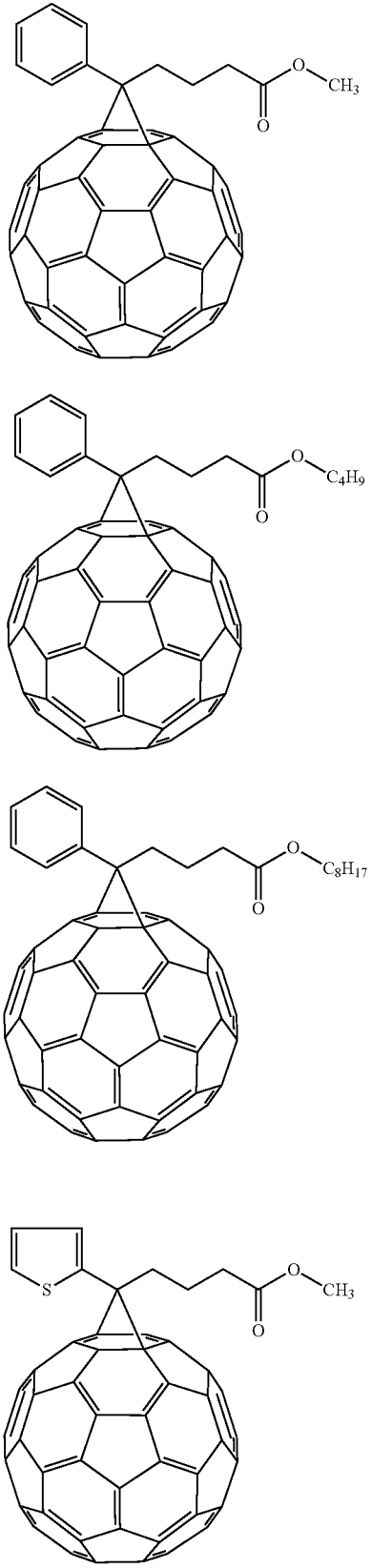

C1: PCBM
C2: PCBB
C3: PCBO
C4: ThCBM
C5: [70]PCBM
C6

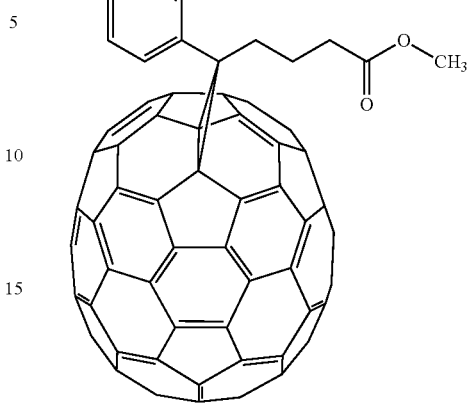

In the photoelectric conversion material of the present invention, the weight ratio of the component (A) to the component (B) (the former:the latter) is from 10:90 to 90:10, preferably from 10:90 to 70:30, more preferably from 20:80 to 50:50.

The photoelectric conversion material of the present invention may contain one kind of solvent or two or more kinds of solvent as necessary.

The solvent is not particularly restricted as long as it can dissolve or disperse the component (A) and the component (B), and examples thereof include water, alcohol solvents, diol solvents, ketone solvents, ester solvents, ether solvents, aliphatic or alicyclic hydrocarbon solvents, aromatic hydrocarbon solvents, hydrocarbon solvents has a cyano group, halogenated hydrocarbon solvents, and other solvents. Photoelectric conversion materials using solvents can be used as coating liquids.

Examples of the above-mentioned alcohol solvents include methanol, ethanol, propanol, isopropanol, 1-butanol, isobutanol, 2-butanol, tertiary butanol, pentanol, isopentanol, 2-pentanol, neopentanol, tertiary pentanol, hexanol, 2-hexanol, heptanol, 2-heptanol, octanol, 2-ethylhexanol, 2-octanol, cyclopentanol, cyclohexanol, cycloheptanol, methylcyclopentanol, methyl cyclohexanol, methylcycloheptanol, benzyl alcohol, ethylene glycol monomethyl ether, ethylene glycol monoethyl ether, propylene glycol monomethyl ether, propylene glucohol monoethyl ether, diethylene glucohol monomethyl ether, diethylene glycol monoethyl ether, triethylene glycol monomethyl ether, triethylene glycol monoethyl ether, 2-(N,N-dimethylamino)ethanol, and 3-(N,N-dimethylamino)propanol.

Examples of the above-mentioned diol solvents include ethylene glycol, propylene glycol, 1,2-butanediol, 1,3-butanediol, 1,4-butanediol, 1,5-pentanediol, neopentyl glycol, isoprene glycol (3-methyl-1,3-butanediol), 1,2-hexandiol, 1,6-hexanediol, 3-methyl-1,5-pentanediol, 1,2-octanediol, octanediol (2-ethyl-1,3-hexandiol), 2-butyl-2-ethyl-1,3-propanediol, 2,5-dimethyl-2,5-hexanediol, 1,2-cyclohexanediol, 1,4-cyclohexanediol, and 1,4-cyclohexanedimethanol.

Examples of the above-mentioned ketone solvents include acetone, ethyl methyl ketone, methyl isopropyl ketone, methyl butyl ketone, methyl isobutyl ketone, methyl amyl ketone, methyl hexyl ketone, ethyl butyl ketone, diethyl ketone, dipropyl ketone, diisobutyl ketone, methyl amyl ketone, cyclohexanone, and methylcyclohexanone.

Examples of the above-mentioned ester solvents include methyl formate, ethyl formate, methyl acetate, ethyl acetate, isopropyl acetate, butyl acetate, isobutyl acetate, secondary butyl acetate, tertiary butyl acetate, amyl acetate, isoamyl acetate, tertiary amyl acetate, phenyl acetate, methyl propionate, ethyl propionate, isopropyl propionate, butyl propionate, isobutyl propionate, secondary butyl propionate, tertiary butyl propionate amyl propionate, isoamyl propionate, tertiary amyl propionate, phenyl propionate, methyl 2-ethylhexanoate, ethyl 2-ethylhexanoate, propyl 2-ethylhexanoate, isopropyl 2-ethylhexanoate, butyl 2-ethylhexanoate, methyl lactate, ethyl lactate, methyl methoxypropionate, methyl ethoxypropionate, ethyl methoxypropionate, ethyl ethoxypropionate, ethylene glycol monomethyl ether acetate, diethylene glycol monomethyl ether acetate, ethylene glycol monoethyl ether acetate, ethylene glycol monopropyl ether acetate, ethylene glycol monoisopropyl ether acetate, ethylene glycol monobutyl ether acetate, ethylene glycol mono-secondary dibutyl ether acetate, ethylene glycol monoisobutyl ether acetate, ethylene glycol mono-tertiary butyl ether acetate, propylene glycol monomethyl ether acetate, propylene glycol monoethyl ether acetate, propylene glycol monopropyl ether acetate, propylene glycol monoisopropyl ether acetate, propylene glycol monobutyl ether acetate, propylene glycol mono-secondary butyl ether acetate, propylene glycol monoisobutyl ether acetate, propylene glycol mono-tertiary butyl ether acetate, butylene glycol monomethyl ether acetate, butylene glycol monoethyl ether acetate, butylene glycol monopropyl ether acetate, butylene glycol monoisopropyl ether acetate, butylene glycol monobutyl ether acetate, butylene glycol mono-secondary butyl ether acetate, butylene glycol monoisobutyl ether acetate, butylene glycol mono-tertiary butyl ether acetate, methyl acetoacetate, ethyl acetoacetate, methyl oxobutanoate, ethyl oxobutanoate, γ-lactone, dimethyl malonate, dimethyl succinate, propylene glycol diacetate, and δ-lactone.

Examples of the above-mentioned ether solvents include tetrahydropyran, tetrahydropyran, morpholine, ethylene glycol dimethyl ether, diethylene glycol dimethyl ether, dipropylene glycol dimethyl ether, triethylene glycol dimethyl ether, dibutyl ether, diethyl ether, and dioxane.

Examples of the above-mentioned aliphatic or alicyclic hydrocarbon solvents include pentane, hexane, cyclohexane, methylcyclohexane, dimethylcyclohexane, ethylcyclohexane, heptane, octane, decalin, solvent naphtha, turpentine oil, D-limonene, pinene, mineral spirit, Swasol #310 (Cosmo Matsuyama Oil Co., Ltd.), and Solvesso #100 (Exxon Chemical).

Examples of the above-mentioned aromatic hydrocarbon solvents include benzene, toluene, ethylbenzene, xylene, mesitylene, diethylbenzene, cumene, isobutylbenzene, cymene, and tetralin.

Examples of the above-mentioned hydrocarbon solvents having a cyano group include acetonitrile, 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene.

Examples of the above-mentioned halogenated hydrocarbon solvents include carbon tetrachloride, chloroform, dichloromethane, trichloroethylene, chlorobenzene, dichlorobenzene, and trichlorobenzene.

Examples of the above-mentioned other organic solvents include N-methyl-2-pyrrolidone, dimethyl sulfoxide, dimethylformamide, aniline, triethylamine, pyridine, and carbon disulfide.

Of these, preferred solvents include chloroform, dichloromethane, toluene, xylene, chlorobenzene, dichlorobenzene, trichlorobenzene, etc.

In the case of including the above-mentioned solvent into the photoelectric conversion material of the present invention, the content thereof, which is not particularly limited as long as the solvent does not disturb the formation of a photoelectric conversion layer using the photoelectric conversion material, can be selected appropriately, for example, from such a range that the total amount of the components (A) and (B) will be 0.1 to 20 parts by weight, more preferably 1 to 10 parts by weight, particularly preferably 3 to 7 parts by weight, per 100 parts by weight of the solvent.

<Photoelectric Conversion Layer>

Next, the photoelectric conversion layer of the present invention is described. The photoelectric conversion layer of the present invention is obtained by forming the photoelectric conversion material of the present invention into a film. The method for the film formation is not particularly restricted and examples thereof include methods of forming a coating film on a support by a dry process, such as a vacuum deposition process, a physical vapor deposition (PVD) process, a chemical vapor deposition (CVD) process, an atomic layer deposition (ALD) process, an atomic layer epitaxy (ALE) process, a molecular beam epitaxy (MBE) process, a vapor phase epitaxy (VPE) process, a sputtering process, and a plasma polymerization process; or a wet process, such as a dip coating process, a casting process, an air knife coating process, a curtain coating process, a roller coating process, a wire bar coating process, a gravure coating process, a spin coating process, an LB process, an offset printing process, a screen printing process, a flexographic printing process, a dispenser printing process, an ink-jet process, and an extrusion die coating process.

The thickness of the photoelectric conversion layer is not particularly limited, but it is generally preferred to set at about 5 nm to about 5 μm, and the photoelectric conversion layer may be subjected to heating treatment such as annealing.

The photoelectric conversion layer is used for an element in which p-type and n-type organic semiconductive materials are mixed, and the layer is used for i-layers in a super hierarchical nanostructure junction element, a hybrid heterojunction type, and a p-i-n junction type element as well as an organic bulk heterojunction element, which is a preferred embodiment.

<Photoelectric Conversion Element and Organic Thin Film Solar Cell>

The photoelectric conversion element of the present invention is configured in the same manner as conventionally known photoelectric conversion elements except that the element has at least one photoelectric conversion layer of the present invention. In a description made by taking FIG.

Figure 1B:
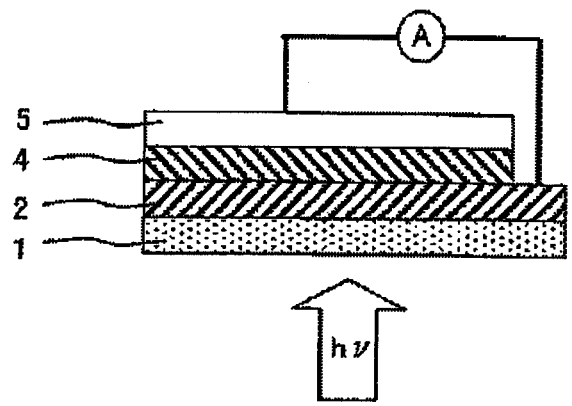
FIG. 1(b) is a cross-sectional view illustrating another example of the configuration of the photoelectric conversion element of the present invention.
Figure 1C:
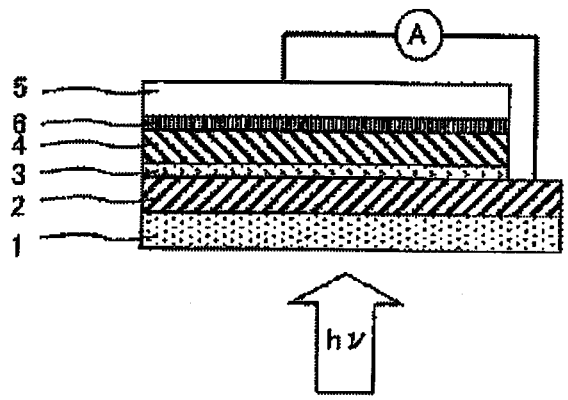
FIG. 1(c) is a cross-sectional view illustrating another example of the configuration of the photoelectric conversion element of the present invention.

1(a) as an example, the photoelectric conversion element of the present invention has a structure in which a support 1, an electrode 2, a charge transfer layer 3, a photoelectric conversion layer 4, and an electrode 5 are laminated in order. A structure in which the charge transfer layer 3 has been removed as depicted in FIG. 1(b) is also adoptable, and a structure further having a charge transfer layer 6 as depicted in FIG. 1(c) is still also adoptable.

In the photoelectric conversion element of the present invention, light is required to reach the photoelectric conversion layer 4 from the support 1. In order to make illuminated light reach to the photoelectric conversion layer 4 from the support 1, the electrode 2, and the charge transfer layer 3, it is preferred to form the support 1, the electrode 2, and the charge transfer layer of a light transmissive material, thereby adjusting the light transmittance to 70% or more.

The support 1 is required to have transparency though the support is not limited with respect to its material or thickness as long as it can stably hold the electrode 2 on its surface. For this reason, the support may be either plate shaped or film shaped. Transparency is a property to allow light in a prescribed wavelength region to be used for photoelectric conversion elements, for example, in the visible region, to pass at high rates. For the support 1, for example, glass, transparent polymer film (polyethylene terephthalate (PET), tetraacetylcellulose (TAC), polycarbonate, polyethylene naphthalate, polyphenylene sulfide, polyester sulfone, syndiotactic polystyrene), etc. can be used. The photoelectric conversion element of the present invention is preferably formed on the surface of the support 1, but when the electrode 2 itself has a certain degree of hardness and has self-supporting property, the element may have a structure in which the electrode 2 serves for the support 1, and in such a case, the support 1 may be omitted.

In the present invention, the work function of a pair of electrodes (the electrode 2 and the electrode 5) oppositely arranged should just have inequality relatively with each other (i.e., have different work functions). Accordingly, the electrode 2 should just be relatively greater in work function than the electrode 5. In this case, the difference between the work functions of the electrodes is preferably 0.5 V or more. When a buffer layer is disposed between each electrode and a semiconductor layer and thereby the compound of the buffer layer on the electrode is chemically bonded to the electrode, such a restriction may be relaxed.

For the electrode 2 and the electrode 5, noble metals such as gold, platinum, and silver, metal oxides such as zinc oxide, indium oxide, tin oxide (NESA), tin-doped indium oxide (ITO), and fluorine-doped tin oxide (FTO), lithium, lithium-indium alloy, sodium, sodium-potassium alloy, calcium, magnesium, magnesium-silver alloy, magnesium-indium alloy, indium, ruthenium, titanium, manganese, yttrium, aluminum, aluminum-lithium alloy, aluminum-calcium alloy, aluminum-magnesium alloy, chromium, graphite thin film as well as organic conductive compounds such as PEDOT-PSS can be used appropriately. These electrode materials each may be used singly or alternatively a plurality of materials may be used in combination. Since the electrode 2 is required to have transparency, materials having transparency, such as zinc oxide, NESA, ITO, FTO, and PEDOT-PSS, are used therefor. The electrode 2 and the electrode 5 can be formed using such electrode materials by a dry process or a wet process in the same manner as that for the above-described photoelectric conversion layer 4. The electrodes also may be formed by calcination by a sol-gel process. Although the thickness of the electrodes depends on the electrode material to be used, it is generally set with both the electrode 2 and the electrode 5 at about 5 to about 1000 nm, preferably about 10 to about 500 nm.

The charge transfer layers 3, 6 have roles of preventing immigration of the electrode materials into photoelectric conversion layers or preventing the electrode materials from reacting, or preventing recombination of charges separated within the photoelectric conversion layers and transferring the charges to the electrodes 2, 5 efficiently. Examples of the materials include charge transfer materials such as PEDOT: PSS, PEO, $V_2O_5$, zinc oxide, lithium fluoride, $TiO_x$, and naphthalene tetracarboxylic anhydride. The charge transfer layer 3 is required to have transparency. When the photoelectric conversion layer 4 is of a bulk hetero type of P3HT:PCBM, PEDOT:PSS is often used for the charge transfer layer 3 and LiF is often used for the charge transfer layer 6. The charge transfer layers 3, 6 can be formed using such charge transfer materials by a dry process or a wet process in the same manner as that for the above-described photoelectric conversion layer 4. The thickness of the charge transfer layers 3, 6 is generally set at 0.01 to 100 nm, preferably about 0.1 to about 50 nm.

The photoelectric conversion element of the present invention can be used for the organic thin film solar cell of the present invention as well as a for photodiode, a photodetector, etc.

Second bibenzo[b]furan compound

The second bibenzo[b]furan compound is represented by the above general formula (B1) or (B2).

The explanations made for the first bibenzo[b]furan compound can be applied to parts that are not explained specifically.

Examples of the optionally substituted hydrocarbon group and the optionally substituted heterocyclic group represented by $R^{13}$ and $R^{14}$ in the above general formula (B2) include groups the same as those of $R^{13}$ and $R^{14}$ in the above general formula (2).

Examples of the optionally substituted hydrocarbon group represented by $R^3$ of $NR^3$ represented by $X^1$ and $X^4$ in Group λ include groups the same as the optionally substituted hydrocarbon group represented by $R^{13}$ and $R^{14}$ in the above general formula (2).

None of the second bibenzo[b]furan compounds is limited with respect to the method for the production thereof, and they can be obtained by methods utilizing reactions well-known in the art. The following is one example of the method for producing the bibenzo[b]furan compounds represented by the above general formula (B1).

First, 3,4:3',4'-bibenzo[b]furan is produced by the method described above. Next, the resulting 3,4:3',4'-bibenzo[b]furan is brominated into dibromobibenzo[b]furan (A). Alternatively, it is also allowed to use a bibenzofuran derivative converted into a halogen compound, a triflate form, a boron compound, a silicon compound, a zinc compound, or a tin compound corresponding thereto.

Subsequently, a desired second bibenzo[b]furan compound can be obtained via a coupling reaction between dibromobibenzo[b]furan (A) with a synthesis intermediate corresponding to $R^{21}$—X— and $R^{22}$—X—.

For some structures of $R^{21}$—X— and $R^{22}$—X—, 3,4:3',4'-bibenzo[b]furan is made to directly undergo a coupling reaction with synthesis intermediates corresponding to $R^{21}$—X— and $R^{22}$—X— without being brominated beforehand.

The second bibenzo[b]furan compound is suited as an intermediate to the first bibenzo[b]furan compound and also can be used for applications such as antioxidants.

EXAMPLES

The present invention is described in more detail below by way of intermediate synthesis examples, examples, and comparative examples. The present invention, however, is not limited at all by the following examples, etc.

Intermediate Synthesis Example 1 provides the synthesis of an intermediate (the above-described dibromobibenzo[b]furan (A)) necessary for the synthesis of a second bibenzo[b]furan compound and Intermediate Synthesis Examples 2 to 5 each provide the synthesis of an intermediate (a second bibenzo[b]furan compound) necessary for the synthesis of a first bibenzo[b]furan compound; Examples 1 to 18 are examples of the synthesis of first bibenzo[b]furan compounds. In Examples 19 to 60 and Comparative Examples 1 to 10, photoelectric conversion materials of the present invention were prepared using the first bibenzo[b]furan compounds obtained in Examples 1 to 18 or comparative compounds and then photoelectric conversion layers and photoelectric conversion elements were prepared using the photoelectric conversion materials, followed by the evaluation of the photoelectric conversion elements.

Intermediate Synthesis Example 1

Synthesis of BBF-Br$_2$: dibromobibenzo[b]furan (A)

<Step 1> Synthesis of Dicarboxylic Acid Form Represented by the Following [Chemical Formula 13]

A solution prepared by charging 25.0 g (0.10 mol) of anthrarufin, 470 ml of 2-butanone, 54.7 g (0.40 mol) of potassium carbonate, and 60.8 g (0.36 mol) of ethyl bromoacetate was heated to 90° C., allowed to react for 6 hours, then cooled to room temperature, followed by the addition of hydrochloric acid, and then filtered. The residue was washed with hydrochloric acid, ultrapure water, and methanol in order and then dried under reduced pressure, affording 42.1 g of brown crystals (yield: 98%).

Subsequently, a solution prepared by charging 36.0 g (0.09 mol) of the brown crystals, 12.1 g (0.30 mol) of sodium hydroxide, 32.0 g of ultrapure water, 65 g of ethanol, and 600 ml of 2-butanone was heated to 90° C., allowed to react for 6 hours, then cooled to room temperature, followed by the addition of hydrochloric acid, and then the residue was filtered. The residue was washed with hydrochloric acid, ultrapure water, and methanol in order and then dried under reduced pressure, affording 30.8 g of yellowish green crystals (yield: 99%). The resulting yellowish green crystals were confirmed with $^1$H-NMR to be the target dicarboxylic acid form. The analysis result is given below.

$^1$H-NMR (DMSO-D6) δ: 13.09 (2H, s), 7.80-7.71 (4H, m), 7.37 (2H, d, J=7.3 Hz), 4.91 (4H, s)

[Chemical Formula 13]

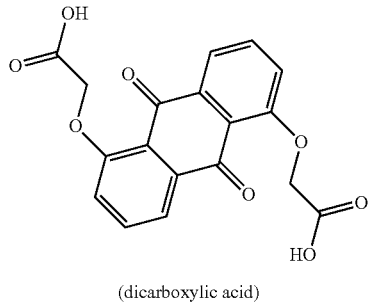

(dicarboxylic acid)

<Step 2> Synthesis of BBF: bibenzo[b]furan

A solution prepared by charging 200 mg (0.56 mmol) of the dicarboxylic acid form obtained in Step 1, 3.6 g of 4-picoline, and 3.3 g of acetic anhydride was heated to 175° C. and then allowed to react for 2 hours. After cooling to 5° C., hydrochloric acid and chloroform were added, followed by separation into oil and water. The organic layer was then washed with a saturated aqueous solution of sodium hydrogen carbonate and ultrapure water in order. The organic layer was dried over magnesium sulfate added thereto and was concentrated under reduced pressure. Thereafter, the formation of BBF was checked with thin layer chromatography (hexane-chloroform). The resulting compound was confirmed with $^1$H-NMR and $^{13}$C-NMR to be the target BBF. Mass analysis was also carried out. The analysis results are given below.

$^1$H-NMR (CDCl$_3$) δ: 7.89 (2H, s), 7.42 (2H, dd, J=5.8 or 2.1 Hz), 7.32 (4H, t, J=3.0 Hz)

$^{13}$C-NMR (CDCl$_3$) δ: 154.13, 137.91, 128.74, 126.39, 123.63, 117.90, 117.17, 110.23

MS (TOF-MS, Dith): m/z 232.2 (100%), 464.3 (8%)

MS (TOF-MS, DHB): m/z 232.2 (100%), 464.3 (14%)

<Step 3> Synthesis of BBF-Br$_2$

Under a nitrogen atmosphere, a solution prepared by charging 1.0 g (4.3 mmol) of the BBF obtained in Step 2 and 22 ml of dimethylformamide (DMF) was cooled to 0° C., and then 15 ml of a DMF solution of 1.8 g (10.3 mmol) of N-bromosuccinimide (NBS) was dropped and stirred for 20 minutes. The temperature was raised to room temperature and then a reaction was carried out for 2 hours, followed by separation into oil and water. The organic layer was then washed with ultrapure water. The organic layer was dried over magnesium sulfate, followed by filtration, concentration under reduced pressure, and purification with silica gel chromatography (developing solvent: hexane-toluene), affording 171 mg of brown crystals (yield: 10%). The resulting grown crystals were confirmed with $^1$H-NMR to be the target BBF-Br$_2$. The analysis result is given below.

$^1$H-NMR (CDCl$_3$) δ: 7.75 (2H, d, J=7.3 Hz), 7.39-7.31 (4H, m)

Intermediate Synthesis Example 2

Synthesis of BBF-3HT Represented by the Following [Chemical Formula 14]

Under a nitrogen atmosphere, a solution prepared by charging 1.0 g (2.56 mmol) of the BBF-Br2 obtained in Intermediate Synthesis Example 1 and 130 ml of toluene was irradiated with ultrasound, and then to the resulting solution were added 2.1 g (7.17 mmol) of 3-hexyl-2-thiopheneboronic acid pinacol ester, 300 mg (0.26 mmol) of tetrakis(triphenylphosphine)palladium, and 6.4 ml (2.0 M, 12.8 mmol) of an aqueous solution of sodium carbonate, followed by the execution of a reaction at 110° C. for 7 hours. Moreover, 1.4 g (4.76 mmol) of 3-hexyl-2-thiopheneboronic acid pinacol ester and 250 mg (0.22 mmol) of tetrakis(triphenylphosphine)palladium were added, followed by the execution of a reaction at 110° C. for 5 hours. Hydrochloric acid and toluene were added, followed by separation into oil and water, and then the organic layer was washed with ultrapure water twice. The organic layer was dried over magnesium sulfate, followed by filtration, concentration under reduced pressure, and purification with silica gel chromatography (developing solvent: hexane-toluene), affording 1.45 g of an yellow oil (yield: 99%). The resulting yellow oil was confirmed with 1H-NMR to be the target BBF-3HT. The analysis result is given below.

$^1$H-NMR (CDCl$_3$) δ: 7.50 (2H, d, J=26.2 Hz), 7.37 (2H, d, J=18.3 Hz), 7.33-7.27 (4H, m), 7.11 (2H, d, J=18.9 Hz), 2.72 (4H, t, J=48.2 Hz), 1.67-1.55 (4H, m), 1.31-1.08 (12H, m), 0.76 (6H, t, J=46.3 Hz)

[Chemical Formula 14]

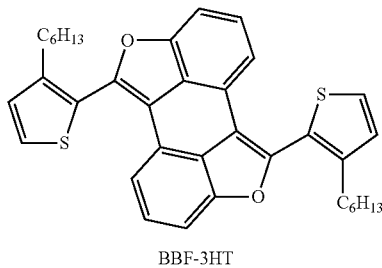

BBF-3HT

Intermediate Synthesis Example 3

Synthesis of BBF-3HTB Represented by the Following [Chemical Formula 15]

To a solution prepared by charging 100 mg (0.24 mmol) of the BBF-3HT obtained in Intermediate Synthesis Example 2 and 6.5 ml of tetrahydrofuran (THF) was added dropwise 1.0 ml of a THF solution of 266 mg (0.71 mmol) of trimethylphenylammonium bromide (PTMA-Br$_3$), followed by stirring at room temperature for 30 minutes. An aqueous solution of sodium thiosulfate and toluene were added, followed by separation into oil and water, and the organic layer was washed with ultrapure water. The organic layer was dried over magnesium sulfate, followed by filtration, concentration under reduced pressure, and purification by silica gel chromatography (developing solvent: hexane-toluene), affording 142 mg of yellow crystals (yield: 99%). The resulting yellow crystals were confirmed with $^1$H-NMR to be the target BBF-3HTB.

$^1$H-NMR (CDCl$_3$) δ: 7.40-7.34 (2H, m), 7.34-7.29 (4H, m), 7.07 (2H, s), 2.64 (4H, t, J=48.8 Hz), 1.64-1.50 (4H, m), 1.28-1.06 (12H, m), 0.76 (6H, t, J=44.5 Hz)

[Chemical Formula 15]

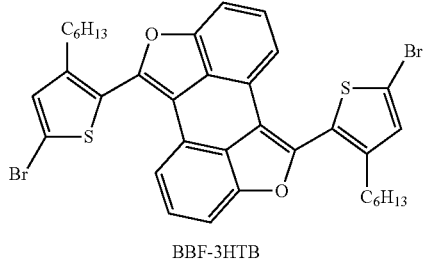

BBF-3HTB

Intermediate Synthesis Example 4

Synthesis of BBF-3HT2B Represented by the Following [Chemical Formula 16]

Under a nitrogen atmosphere, a solution prepared by charging 0.19 g (0.33 mmol) of the BBF-3HTB synthesized in Intermediate Synthesis Example 3 and 20 ml of toluene was irradiated with ultrasound, and then to the resulting solution were added 0.26 g (0.92 mmol) of 3-hexyl-2-thiopheneboronic acid pinacol ester, 38 mg (0.033 mmol) of tetrakis(triphenylphosphine)palladium, and 0.83 ml (2 M, 1.65 mmol) of an aqueous solution of sodium carbonate, followed by the execution of a reaction at 110° C. for 8 hours. Moreover, 0.17 g (0.61 mmol) of 3-hexyl-2-thiopheneboronic acid pinacol ester and 32 mg (0.027 mmol) of tetrakis(triphenylphosphine)palladium were added, followed by the execution of a reaction at 110° C. for 5 hours. Hydrochloric acid and toluene were added, followed by separation into oil and water, and then the organic layer was washed with ultrapure water twice. The organic layer was dried over magnesium sulfate, followed by filtration, concentration under reduced pressure, and purification by silica gel column chromatography. The purified product was dissolved in 9 ml of tetrahydrofuran (THF) and then 1.3 ml of a THF solution of 355 mg (0.95 mmol) of trimethylphenylammonium bromide (PTMA-Br$_3$) was added dropwise, followed by stirring at room temperature for 30 minutes. An aqueous solution of sodium thiosulfate and toluene were added, followed by separation into oil and water, and the organic layer was washed with ultrapure water. The organic layer was dried over magnesium sulfate, followed by filtration, concentration under reduced pressure, and purification by silica gel chromatography (developing solvent: hexane-toluene), affording 0.24 g of orange crystalline BBF-3HT2B (yield: 93%). Identification was carried out by $^1$H-NMR. The analysis results are given below.

$^1$H-NMR (CDCl$_3$) δ: 7.54-7.44 (2H, m), 7.37-7.27 (4H, m), 7.05 (2H, s), and 6.94 (2H, s), 2.78 (4H, t, J=27.4 Hz) and 2.71 (4H, t, J=26.8 Hz), 1.71-1.58 (8H, m), 1.45-1.12 (24H, m), 0.88 (6H, t, J=37.2 Hz), 0.77 (6H, t, J=26.2 Hz)

[Chemical Formula 16]

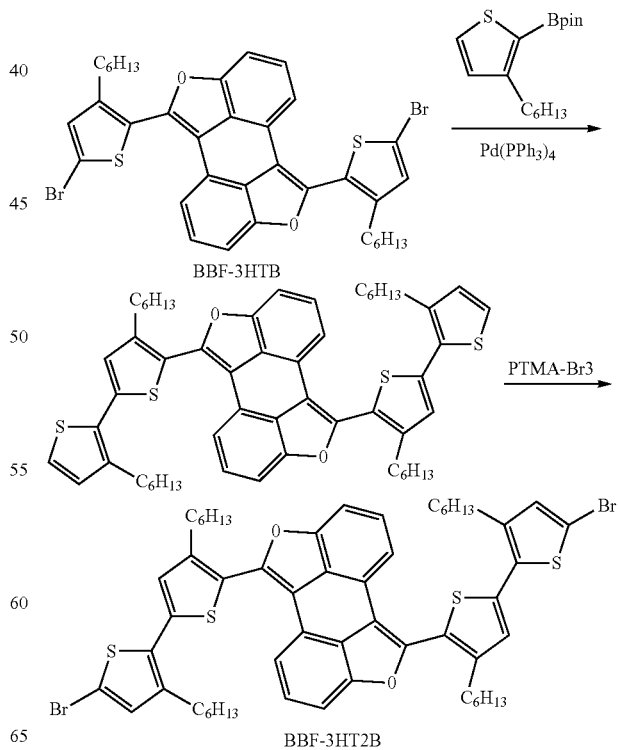

BBF-3HTB

BBF-3HT2B

Intermediate Synthesis Example 5

Synthesis of BBF-4HTB Represented by the Following [Chemical Formula 17]

A reaction was carried out in the same procedures as in Intermediate Synthesis Example 2 except that the 3-hexyl-2-thiopheneboronic acid pinacol ester used in Intermediate Synthesis Example 2 was changed to 4-hexyl-2-thiopheneboronic acid pinacol ester to form BBF-4HT, and then bromination was carried out in the same procedures as in Intermediate Synthesis Example 3, affording 141 mg of yellow crystalline BBF-4HTB (yield: 99%). Identification was carried out by $^1$H-NMR. The analysis results are given below.

$^1$H-NMR (CDCl$_3$) δ: 7.91 (2H, d, J=30.5 Hz), 7.48 (2H, s), 7.34 (4H, q, J=50.0 Hz), 2.68 (4H, t, J=59.1 Hz), 1.78-1.63 (4H, m), 1.49-1.29 (12H, m), 0.92 (6H, t, J=78.7 Hz)

[Chemical Formula 17]

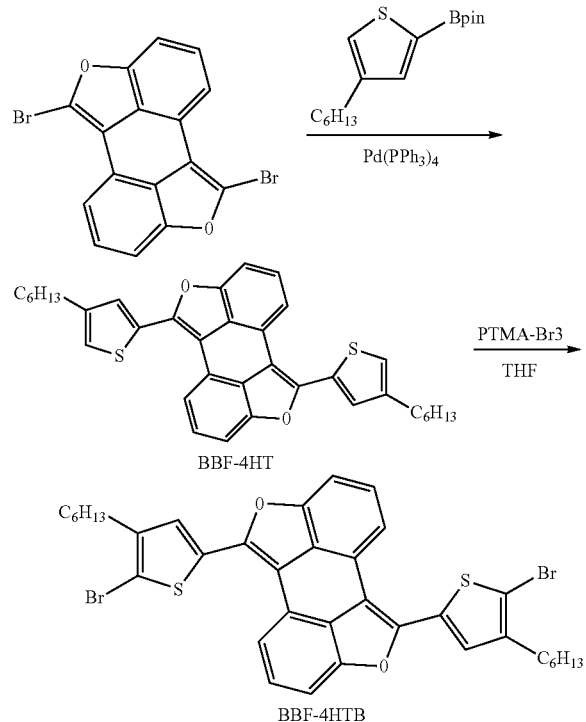

Example 1

Synthesis of Compound No. 5

Under a nitrogen atmosphere, a solution prepared by charging 180 mg (0.25 mmol) of the BBF-3HTB synthesized in Intermediate Synthesis Example 3 and 10 ml of toluene was irradiated with ultrasound, and then to the resulting solution were added 97 mg (0.21 mmol) of 2,1,3-benzothiadiazole-4,7-bis(boronic acid pinacol ester), 11 mg (0.013 mmol) of tris(dibenzylidene acetone)dipalladium, 23 mg (0.075 mmol) of tri(o-tolyl)phosphine, and 1.7 ml (2.0 M, 3.4 mmol) of an aqueous solution of sodium carbonate, followed by the execution of a reaction at 120° C. for 6 hours. Moreover, 11 mg (0.013 mmol) of tris(dibenzylidene acetone)dipalladium and 23 mg (0.075 mmol) of tri(o-tolyl)phosphine were added, followed by the execution of a reaction at 120° C. for 6 hours. Reprecipitation was conducted by the addition of methanol, and the resulting residue was washed with methanol and ultrapure water in order and then refluxed in acetone. The solution was filtered, washed with acetone, and then dried, affording 126 mg of dark purple crystalline Compound No. 5 (yield: 99%). The resulting Compound No. 5 had a number average molecular weight (Mn) of 3638, a weight average molecular weight (Mw) of 5800, and Mw/Mn of 1.59.

Example 2

Synthesis of Compound No. 6

Under a nitrogen atmosphere, 580 mg (3.58 mmol) of iron(III) chloride was added to a solution prepared by charging 300 mg (0.53 mmol) of the BBF-3HT synthesized in Intermediate Synthesis Example 2 and 53 ml of chloroform, followed by the execution of a reaction at room temperature for 40 hours. After adding hydrazine monohydrate and stirring for 4 hours, reprecipitation was conducted by the addition of methanol, and the resulting residue was washed with methanol and ultrapure water in order and then refluxed in acetone. The resulting residue was dried, affording 390 mg of dark red solid Compound No. 6 (yield: 95%). The resulting Compound No. 6 had a number average molecular weight (Mn) of 6236, a weight average molecular weight (Mw) of 15437, and Mw/Mn of 2.47.

Example 3

Synthesis of Compound No. 7

Under a nitrogen atmosphere, a solution prepared by charging 200 mg (0.19 mmol) of the BBF-3HT2B synthesized in Intermediate Synthesis Example 4, 81 mg 0.21 mmol) of 2,1,3-benzothiadiazole-4,7-bis(boronic acid pinacol ester), and 15 ml of toluene was irradiated with ultrasound, and then to the resulting solution were added 22 mg (0.019 mmol) of tetrakis(triphenylphosphine)palladium and 8.0 ml (2.0 M, 16.0 mmol) of an aqueous solution of sodium carbonate, followed by the execution of a reaction at 90° C. for 12 hours. Subsequently, 232 mg (1.9 mmol) of phenylboronic acid and 11 mg (0.001 mmol) of tetrakis(triphenylphosphine)palladium were added, followed by the execution of a reaction at 90° C. for 4 hours, and moreover 298 mg (1.9 mmol) of phenyl bromide and 11 mg (0.001 mmol) of tetrakis(triphenylphosphine)palladium were added, followed by the execution of a reaction at 90° C. for 4 hours. After cooling to room temperature, reprecipitation was conducted by the addition of methanol, and the resulting residue was washed with methanol and ultrapure water in order. Additionally, the residue was washed with acetone for 9 hours by using a Soxhlet extractor and then dried, affording 143 mg of dark purple crystalline Compound No. 7 (yield: 72%). The resulting Compound No. 7 had a number average molecular weight (Mn) of 2980, a weight average molecular weight (Mw) of 4073, and Mw/Mn of 1.37.

Examples 4 to 18

Synthesis of Compound Nos. 8 to 11, 13, 14, 29, and 71 to 78

In the same procedures as used in Example 3, Compound Nos. 8 to 11, Compound No. 13, Compound No. 14, Compound No. 29 and Compound Nos. 71 to 78 were synthesized. The yields and the molecular weights are given in Table 1.

TABLE 1

| Example | Compound | Yield/% | Mn | Mw | Mw/Mn |
|---|---|---|---|---|---|
| Example 1 | Compound No. 5 | 99 | 3638 | 5800 | 1.59 |
| Example 2 | Compound No. 6 | 95 | 6236 | 15437 | 2.47 |
| Example 3 | Compound No. 7 | 72 | 2980 | 4073 | 1.37 |
| Example 4 | Compound No. 8 | 95 | 15343 | 36707 | 2.39 |
| Example 5 | Compound No. 9 | 85 | 1516 | 3427 | 2.26 |
| Example 6 | Compound No. 10 | 31 | 5697 | 12382 | 2.17 |
| Example 7 | Compound No. 11 | 8 | 1050 | 1605 | 1.53 |
| Example 8 | Compound No. 13 | 59 | 5142 | 9644 | 1.88 |
| Example 9 | Compound No. 14 | 33 | 9016 | 108385 | 12.0 |
| Example 10 | Compound No. 29 | 71 | 14199 | 63605 | 4.48 |
| Example 11 | Compound No. 71 | 16 | 14988 | 45919 | 3.06 |
| Example 12 | Compound No. 72 | 16 | 6697 | 10947 | 1.63 |
| Example 13 | Compound No. 73 | 2 | 9463 | 15683 | 1.66 |
| Example 14 | Compound No. 74 | 41 | 5718 | 9308 | 1.63 |
| Example 15 | Compound No. 75 | 63 | 12608 | 29368 | 2.33 |
| Example 16 | Compound No. 76 | 60 | 5576 | 10285 | 1.84 |
| Example 17 | Compound No. 77 | 40 | 1498 | 2433 | 1.62 |
| Example 18 | Compound No. 78 | 31 | 7352 | 12356 | 1.68 |

Example 19

A photoelectric conversion device having the layer structure depicted in FIG. 1(c) was produced in the following procedures. A glass substrate (a support 1) on which ITO had been formed into a film in a thickness of 150 nm as an electrode 2 was boiled and washed in IPA and also washed with UV-ozone, then PEDOT:PSS (3,4-ethylene dioxythiophene:polystyrene sulfonic acid) was formed into a film as a charge transfer layer 3 by a spin coating method and then dried under reduced pressure at 100° C. for 10 minutes. The photoelectric conversion material of Example 19 was prepared by dissolving 20 mg of the compound of Example 1 as a p-type organic semiconductor (A) and 80 mg of PCBM as an n-type organic semiconductor (B) in 2 mL of 1,2-dichlorobenzene. The photoelectric conversion material prepared was processed into a film by spin coating and then dried under reduced pressure at 100° C. for 30 minutes to form a photoelectric conversion layer 4. On the thus-obtained organic thin film layer, 0.5 nm thick LiF (charge transfer layer 6) and 100 nm thick aluminum (electrode 5) were formed sequentially by vacuum vapor deposition using a metal mask, so that the photoelectric conversion element of Example 19 was prepared.

The thus-obtained photoelectric conversion element was irradiated with false sunlight of an air mass of 1.5 G and 100 mW/cm$^2$ from its ITO electrode side and thereby its photoelectric conversion characteristic (efficiency (%)) was measured. The result is given in Table 2.

Examples 20 to 60

The photoelectric conversion elements of Examples 20 to 60 were prepared in the same procedures as in Example 19 except that component (A), component (B) and their proportions were changed as shown in Table 2. In addition, the photoelectric transfer characteristic (efficiency (%)) of the photoelectric conversion elements of Examples 20 to 60 was measured by the same operation as in Example 19. The results are given in Table 2.

Comparative Examples 1 to 10

The photoelectric conversion elements of Comparative Examples 1 to 10 were prepared in the same operation as in Example 19 using Comparative Compound Nos. 1 to 4 given in the following [Chemical Formula 18] as component (A) instead of the compound of the present invention according to the compounding amounts given in Table 3 in the preparation of the photoelectric conversion element of the above-described Example 19, and then the photoelectric conversion characteristic (efficiency (%)) of the photoelectric conversion elements of Comparative Examples 1 to 10 was measured in the same operation as in Example 19. The results are shown in [Table 3].

TABLE 2

| | Component (A) | Component (B) | (A)/(B) | Conversion efficiency (%) |
|---|---|---|---|---|
| Example 19 | Compound No. 5 | PCBM | 1/4 | 0.30 |
| Example 20 | Compound No. 6 | PCBM | 1/4 | 0.30 |
| Example 21 | Compound No. 6 | [70]PCBM | 1/4 | 0.54 |
| Example 22 | Compound No. 9 | [70]PCBM | 1/4 | 0.51 |
| Example 23 | Compound No. 10 | PCBM | 1/1 | 0.23 |
| Example 24 | Compound No. 10 | PCBM | 1/2 | 0.46 |
| Example 25 | Compound No. 10 | PCBM | 1/4 | 0.50 |
| Example 26 | Compound No. 10 | [70]PCBM | 1/2 | 0.41 |
| Example 27 | Compound No. 10 | [70]PCBM | 1/4 | 1.05 |
| Example 28 | Compound No. 11 | [70]PCBM | 1/2 | 0.30 |
| Example 29 | Compound No. 13 | [70]PCBM | 1/2 | 0.33 |
| Example 30 | Compound No. 13 | [70]PCBM | 1/4 | 0.29 |
| Example 31 | Compound No. 14 | [70]PCBM | 1/4 | 0.37 |
| Example 32 | Compound No. 14 | [70]PCBM | 1/8 | 0.36 |
| Example 33 | Compound No. 29 | PCBM | 1/2 | 0.50 |
| Example 34 | Compound No. 29 | PCBM | 1/4 | 0.86 |
| Example 35 | Compound No. 29 | [70]PCBM | 1/2 | 0.87 |
| Example 36 | Compound No. 29 | [70]PCBM | 1/4 | 3.03 |
| Example 37 | Compound No. 71 | PCBM | 1/2 | 0.38 |
| Example 38 | Compound No. 71 | [70]PCBM | 1/2 | 0.76 |
| Example 39 | Compound No. 72 | PCBM | 1/2 | 0.42 |
| Example 40 | Compound No. 72 | PCBM | 1/4 | 0.43 |
| Example 41 | Compound No. 72 | [70]PCBM | 1/2 | 1.49 |
| Example 42 | Compound No. 72 | [70]PCBM | 1/4 | 0.67 |
| Example 43 | Compound No. 73 | [70]PCBM | 1/4 | 0.67 |
| Example 44 | Compound No. 74 | PCBM | 1/2 | 0.59 |
| Example 45 | Compound No. 74 | PCBM | 1/4 | 0.38 |
| Example 46 | Compound No. 74 | [70]PCBM | 1/2 | 1.06 |
| Example 47 | Compound No. 74 | [70]PCBM | 1/4 | 1.10 |
| Example 48 | Compound No. 75 | PCBM | 1/2 | 1.09 |
| Example 49 | Compound No. 75 | PCBM | 1/4 | 0.70 |
| Example 50 | Compound No. 75 | [70]PCBM | 1/2 | 1.01 |
| Example 51 | Compound No. 75 | [70]PCBM | 1/4 | 0.79 |
| Example 52 | Compound No. 76 | PCBM | 1/2 | 0.63 |
| Example 53 | Compound No. 76 | PCBM | 1/4 | 0.45 |
| Example 54 | Compound No. 76 | [70]PCBM | 1/2 | 0.93 |
| Example 55 | Compound No. 76 | [70]PCBM | 1/4 | 0.64 |
| Example 56 | Compound No. 77 | PCBM | 1/4 | 0.24 |
| Example 57 | Compound No. 78 | PCBM | 1/2 | 0.35 |
| Example 58 | Compound No. 78 | PCBM | 1/4 | 0.46 |
| Example 59 | Compound No. 78 | [70]PCBM | 1/2 | 0.32 |
| Example 60 | Compound No. 78 | [70]PCBM | 1/4 | 1.12 |

TABLE 3

| | Component (A) | Component (B) | (A)/(B) | Conversion efficiency (%) |
|---|---|---|---|---|
| Comparative Example 1 | Comparative Compound No. 1 | PCBM | 1/4 | 0.18 |
| Comparative Example 2 | Comparative Compound No. 2 | PCBM | 1/1 | 0.02 |
| Comparative Example 3 | Comparative Compound No. 3 | PCBM | 1/4 | 0.06 |
| Comparative Example 4 | Comparative Compound No. 3 | PCBM | 1/2 | 0.11 |
| Comparative Example 5 | Comparative Compound No. 3 | [70]PCBM | 1/4 | 0.0003 |

TABLE 3-continued

| | Component (A) | Component (B) | (A)/(B) | Conversion efficiency (%) |
|---|---|---|---|---|
| Comparative Example 6 | Comparative Compound No. 3 | [70]PCBM | 1/1 | 0.004 |
| Comparative Example 7 | Comparative Compound No. 4 | PCBM | 1/4 | 0.05 |
| Comparative Example 8 | Comparative Compound No. 4 | PCBM | 1/1 | 0.09 |
| Comparative Example 9 | Comparative Compound No. 4 | [70]PCBM | 1/4 | 0.07 |
| Comparative Example 10 | Comparative Compound No. 4 | [70]PCBM | 1/1 | 0.09 |

[Chemical Formula 18]

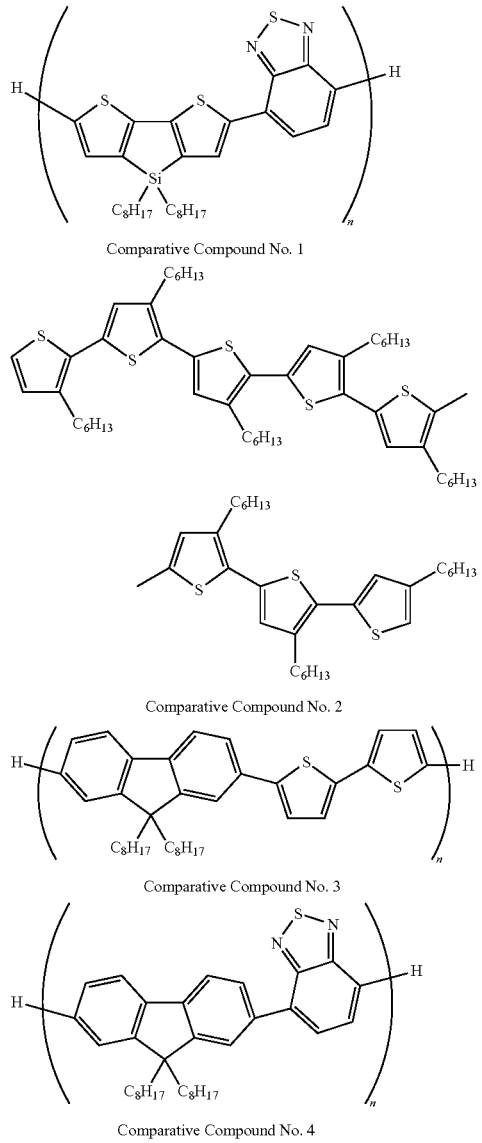

Comparative Compound No. 1: produced by 1-Material, number average molecular weight: 55000
Comparative Compound No. 2: a product synthesized by the applicant company.
Comparative Compound No. 3: produced by Aldrich, number average molecular weight >20000
Comparative Compound No. 4: produced by Aldrich, number average molecular weight: 10000 to 20000

The results described above successfully confirmed that the bibenzo[b]furan compound of the present invention exerts high photoelectric conversion efficiency when being used as a p-type organic semiconductor. Although odor was detected during film formation in Comparative Example 2, no odor was confirmed in the Examples and therefore environmental loading was expected to be low.

Therefore, photoelectric conversion materials using the bibenzo[b]furan compounds of the present invention are useful for photoelectric conversion elements and organic thin film solar cells.

The invention claimed is:

1. A bibenzo[b]furan compound having 2 to 100 constitutional units represented by the formula (1) or (2):

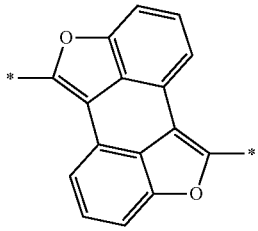
(1)

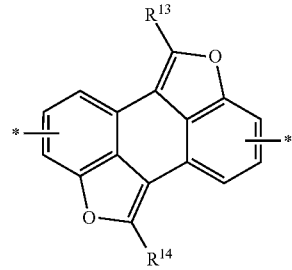
(2)

wherein $R^{13}$ and $R^{14}$ each represent a hydrogen atom, a fluorine atom, a chlorine atom, a bromine atom, an iodine atom, an optionally substituted hydrocarbon group, or an optionally substituted heterocyclic group, and at least one constitutional unit selected from the following Group Y or the following Group Z:

Group Y

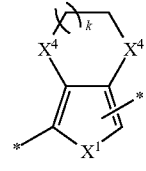
(Y-6)

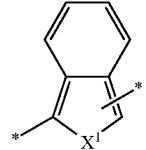
(Y-7)

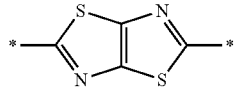
(Y-8)

wherein $X^1$ and $X^4$ each represent S, O, or $NR^3$, k represents an integer of 1 to 4, $R^3$ represents an optionally substituted hydrocarbon group, any hydrogen atom in the constitutional units represented by Group Y may be substituted with a fluorine atom, a chlorine atom, a bromine atom, an iodine atom, a cyano group, a nitro group, a hydroxyl group, a thiol group, an —NR⁴R⁵ group, an optionally substituted hydrocarbon group, or an optionally substituted heterocyclic group, $R^4$ and $R^5$ each represent an optionally substituted hydrocarbon group,
Group Z
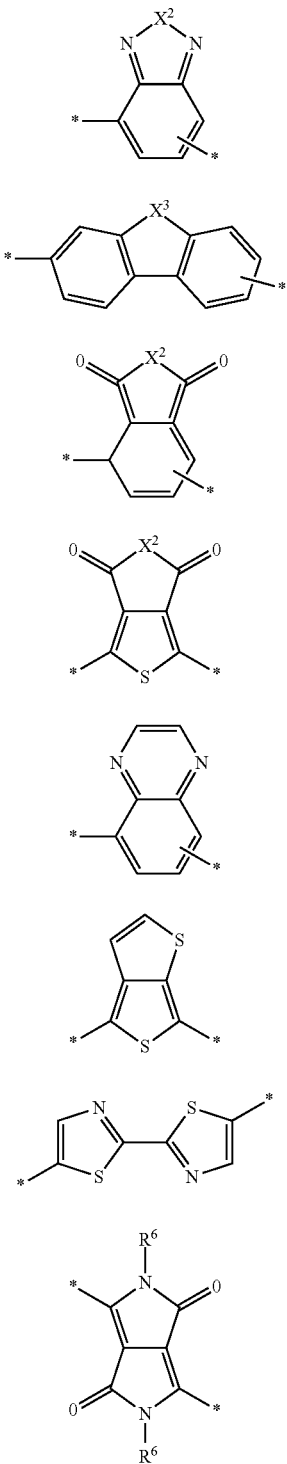
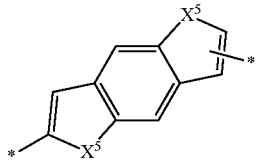
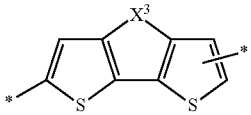
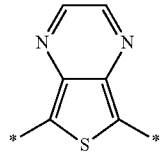
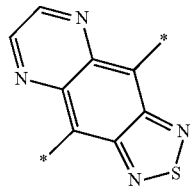
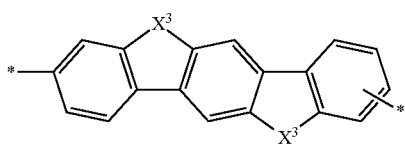
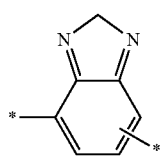
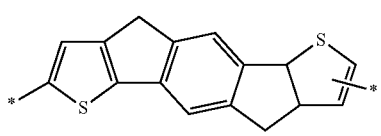
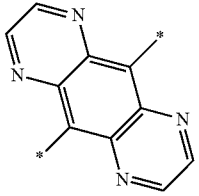
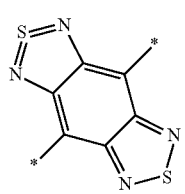

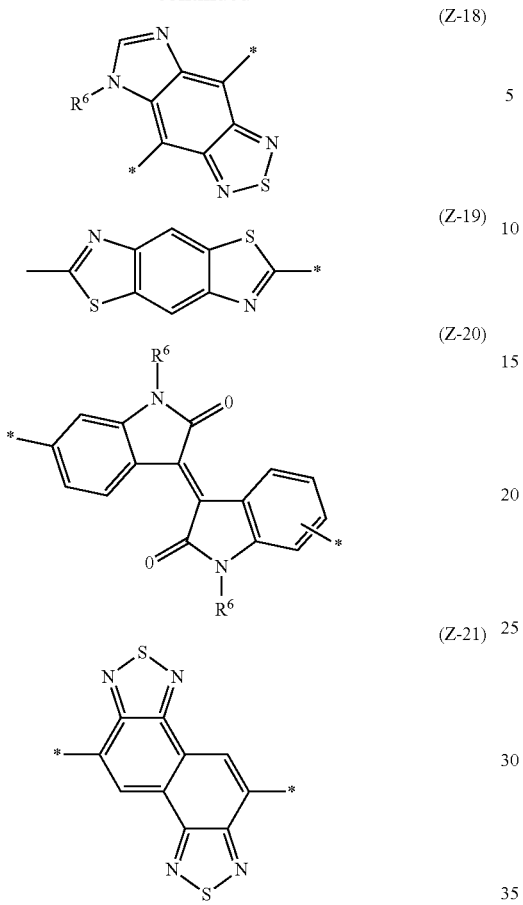

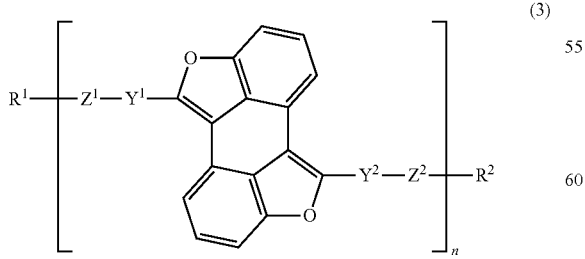

wherein $X^2$ represents S or $NR^6$, $X^3$ represents S, $NR^6$, $CR^7R^8$, or $SiR^7R^8$, $X^5$ represents S, O, or $NR^6$, $R^6$, $R^7$, and $R^8$ each represent an optionally substituted hydrocarbon group, any hydrogen atom in the constitutional units represented by Group Z may be substituted with a fluorine atom, a chlorine atom, a bromine atom, an iodine atom, a cyano group, a nitro group, a hydroxyl group, a thiol group, an —$NR^9R^{10}$ group, an optionally substituted hydrocarbon group, or an optionally substituted heterocyclic group, $R^9$ and $R^{10}$ each represent an optionally substituted hydrocarbon group.

2. The bibenzo[b]furan compound according to claim 1, wherein the compound is represented by the following formula (3) or (4):

(3)

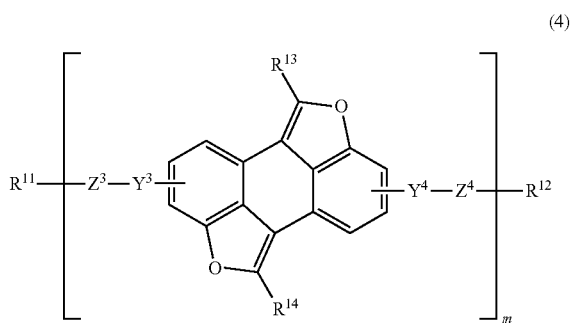

wherein $R^1$ and $R^2$ each represent a hydrogen atom, a fluorine atom, a chlorine atom, a bromine atom, an iodine atom, an optionally substituted hydrocarbon group, or an optionally substituted heterocyclic group, $Y^1$ and $Y^2$ each represent a single bond or a group formed by linking 1 to 5 types of group selected from among the following (Y-1) to (Y-8) in combination, $Z^1$ and $Z^2$ each represent a single bond or a group selected from among the following (Z-1) to (Z-21), n represents an integer of 2 to 100, (4)

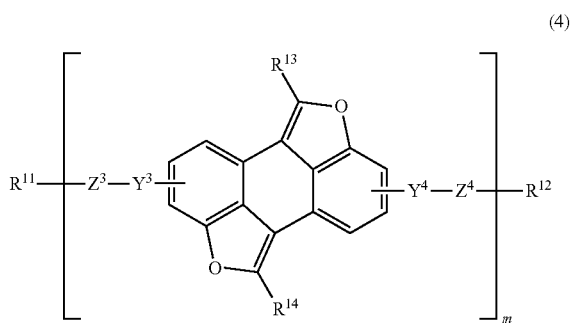

wherein $R^{11}$, $R^{12}$, $R^{13}$, or $R^{14}$ represents a hydrogen atom, a fluorine atom, a chlorine atom, a bromine atom, an iodine atom, an optionally substituted hydrocarbon group, or an optionally substituted heterocyclic group, $Y^3$ and $Y^4$ each represent a single bond or a group formed by linking 1 to 5 types of group selected from among the following (Y-1) to (Y-8) in combination, $Z^3$ and $Z^4$ each represent a single bond or a group selected from among the following (Z-1) to (Z-21), and m represents an integer of 2 to 100, (Y-6)

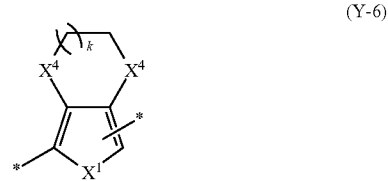

(Y-7)

(Y-8)

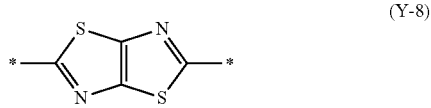

wherein $X^1$ and $X^4$ each represent S, O, or $NR^3$, k represents an integer of 1 to 4, $R^3$ represents an optionally substituted hydrocarbon group, any hydrogen group in (Y-1) to (Y-4) and (Y-6) to (Y-8) may be substituted with a fluorine group, a chlorine atom, a bromine atom, an iodine atom, a cyano group, a nitro group, a hydroxyl group, a thiol group, an —$NR^4R^5$ group, an optionally substituted hydrocarbon group, or an optionally substituted heterocyclic group, $R^4$ and $R^5$ each represent an optionally substituted hydrocarbon group,

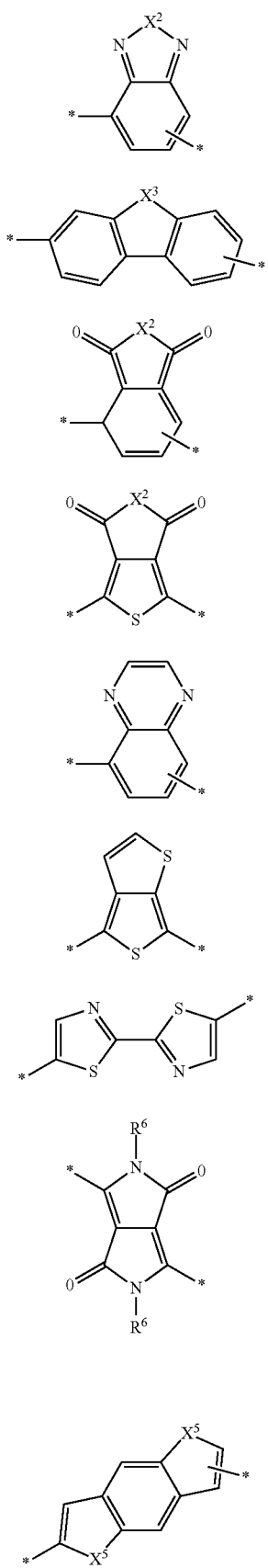
(Z-1)
(Z-2)
(Z-3)
(Z-4)
(Z-5)
(Z-6)
(Z-7)
(Z-8)
(Z-9)
-continued
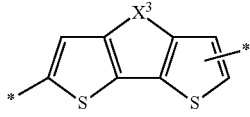 (Z-10)
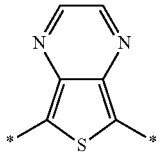 (Z-11)
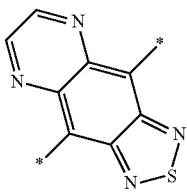 (Z-12)
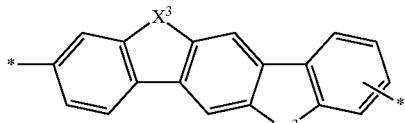 (Z-13)
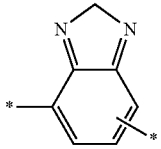 (Z-14)
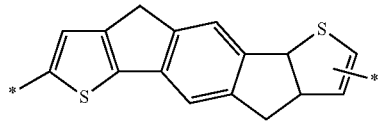 (Z-15)
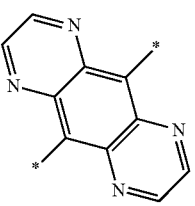 (Z-16)
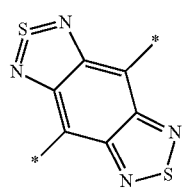 (Z-17)
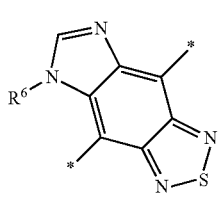 (Z-18)

-continued

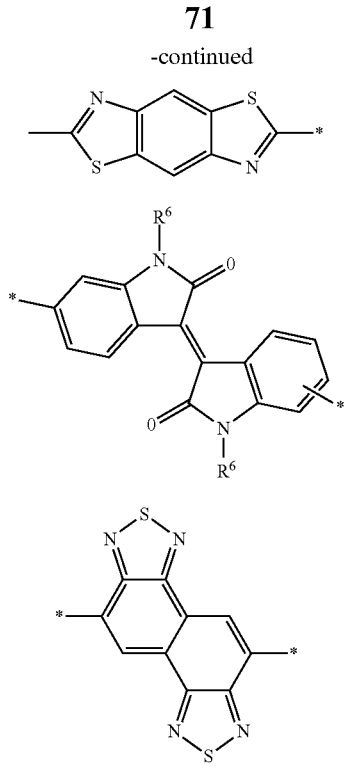

(Z-19)

(Z-20)

(Z-21)

wherein $X^2$ represents S, $NR^6$, or $SiR^7R^8$, $X^3$ represents S, $NR^6$, $CR^7R^8$, or $SiR^7R^8$, $X^5$ represents S, O, or $NR^6$, $R^6$, $R^7$, and $R^8$ each represent an optionally substituted hydrocarbon group, any hydrogen atom in the (Z-1) to (Z-21) groups may be substituted with a fluorine atom, a chlorine atom, a bromine atom, an iodine atom, a cyano group, a nitro group, a hydroxyl group, a thiol group, an —$NR^9R^{10}$ group, an optionally substituted hydrocarbon group, or an optionally substituted heterocyclic group, $R^9$ and $R^{10}$ each represent an optionally substituted hydrocarbon group.

3. A photoelectric conversion material comprising (A) a p-type organic semiconductive material comprising at least one bibenzo[b]furan compound according to claim 1 and (B) an n-type organic semiconductive material.

4. A photoelectric conversion layer obtained by forming the photoelectric conversion material according to claim 3 into a film.

5. A photoelectric conversion element comprising the photoelectric conversion layer according to claim 4.

6. An organic thin film solar cell comprising the photoelectric conversion element according to claim 5.

7. A bibenzo[b]furan compound represented by the following formula (B1) or (B2):

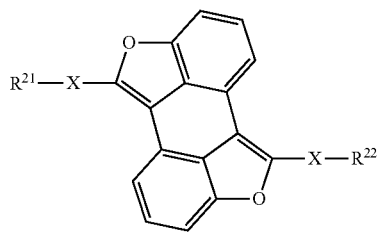

(B1)

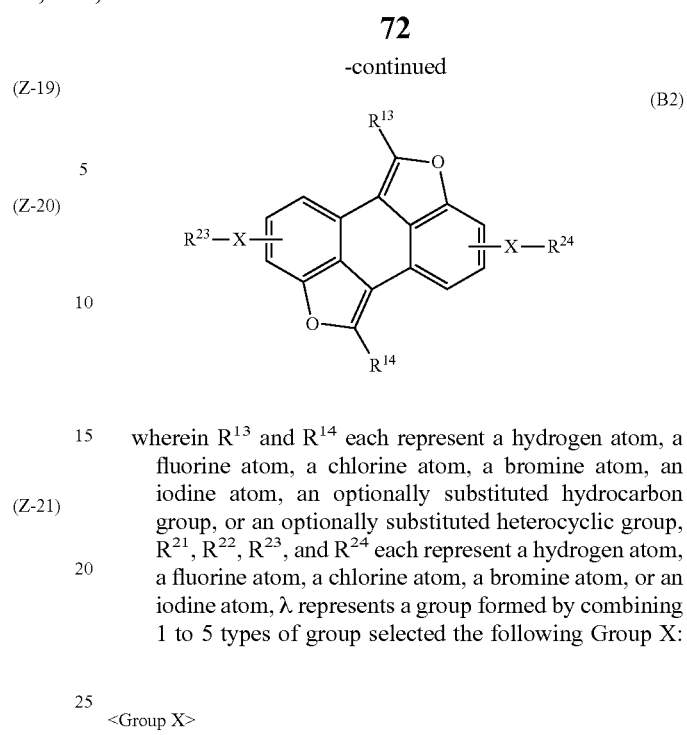

(B2)

wherein $R^{13}$ and $R^{14}$ each represent a hydrogen atom, a fluorine atom, a chlorine atom, a bromine atom, an iodine atom, an optionally substituted hydrocarbon group, or an optionally substituted heterocyclic group, $R^{21}$, $R^{22}$, $R^{23}$, and $R^{24}$ each represent a hydrogen atom, a fluorine atom, a chlorine atom, a bromine atom, or an iodine atom, λ represents a group formed by combining 1 to 5 types of group selected the following Group X:

<Group X>

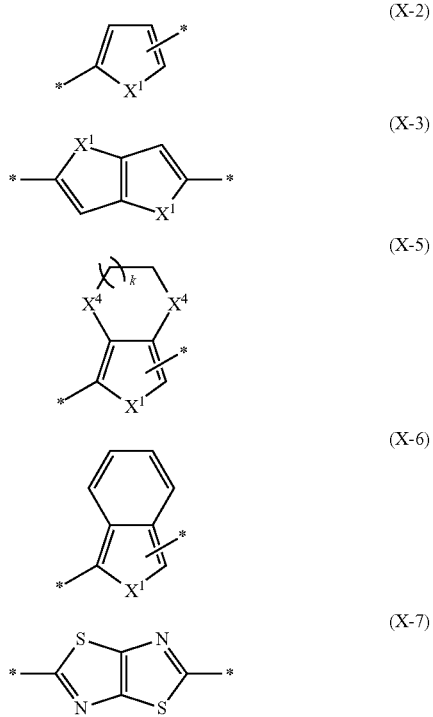

(X-2)

(X-3)

(X-5)

(X-6)

(X-7)

wherein $X^1$ and $X^4$ each represent S, O, or $NR^3$, $R^3$ represents an optionally substituted hydrocarbon group, any hydrogen atom in the constitutional units represented by Group λ may be substituted with a fluorine atom, a chlorine atom, a bromine atom, an iodine atom, a cyano group, a nitro group, a hydroxyl group, a thiol group, an —$NR^4R^5$ group, an optionally substituted hydrocarbon group, or an optionally substituted heterocyclic group, $R^4$ and $R^5$ each represent an optionally substituted hydrocarbon group, k represents an integer of 1 to 4.

8. A photoelectric conversion material comprising (A) a p-type organic semiconductive material comprising at least one bibenzo[b]furan compound according to claim 2 and (B) an n-type organic semiconductive material.

* * * * *